(12) United States Patent
Nguyen et al.

(10) Patent No.: US 9,936,939 B2
(45) Date of Patent: Apr. 10, 2018

(54) TISSUE REPAIR DEVICES

(75) Inventors: Linh Tuong Nguyen, Randolph, MA (US); Paul Steven Vincuilla, Brockton, MA (US); Richard Mark Lunn, Kingston, MA (US); Mark Edwin Housman, North Attleborough, MA (US); Matthew Edwin Koski, Westford, MA (US); Roland Francis Gattuma, East Bridgewater, MA (US); David A. Paulk, Hopedale, MA (US)

(73) Assignee: Smith & Nephew, Inc., Memphis, TN (US)

( * ) Notice: Subject to any disclaimer, the term of this patent is extended or adjusted under 35 U.S.C. 154(b) by 357 days.

(21) Appl. No.: 12/943,086

(22) Filed: Nov. 10, 2010

(65) Prior Publication Data

US 2011/0112576 A1    May 12, 2011

Related U.S. Application Data

(60) Provisional application No. 61/259,737, filed on Nov. 10, 2009, provisional application No. 61/259,739, (Continued)

(51) Int. Cl.
*A61B 17/04* (2006.01)

(52) U.S. Cl.
CPC .... *A61B 17/0401* (2013.01); *A61B 2017/044* (2013.01); *A61B 2017/0409* (2013.01); *A61B 2017/0412* (2013.01); *A61B 2017/0414* (2013.01); *A61B 2017/0435* (2013.01); *A61B 2017/0441* (2013.01);
(Continued)

(58) Field of Classification Search
CPC ........... A61F 2002/0864; A61B 17/864; A61B 17/8645; A61B 17/0401; A61B 2017/0414; A61B 2017/0424; A61B 2017/0446; A61B 2017/0462; A61B 2017/0445;
(Continued)

(56) References Cited

U.S. PATENT DOCUMENTS

| 254,473 A | 3/1882 | Gates |
| 3,187,620 A | 6/1965 | Fischer |

(Continued)

FOREIGN PATENT DOCUMENTS

| DE | 200007777 | 8/2000 |
| DE | 102008016607 A1 | 7/2009 |

(Continued)

OTHER PUBLICATIONS

International Search and Written Opinion for PCT/US2010/056107 dated May 25, 2011.
(Continued)

*Primary Examiner* — Alexander Orkin
(74) *Attorney, Agent, or Firm* — Norman F. Hainer, Jr.

(57) ABSTRACT

The present disclosure relates to an anchor assembly. The anchor assembly includes an anchor defining a cavity and an opening to the cavity; and a headless insertion member configured for arrangement within the anchor cavity, the insertion member including a body having a threaded proximal portion, a non-threaded distal portion, and a cannulation extending a partial length of the insertion member. Other anchor assemblies, anchors, and delivery devices are also disclosed.

18 Claims, 42 Drawing Sheets

Related U.S. Application Data filed on Nov. 10, 2009, provisional application No. 61/290,695, filed on Dec. 29, 2009, provisional application No. 61/312,481, filed on Mar. 10, 2010, provisional application No. 61/334,221, filed on May 13, 2010.

(52) U.S. Cl.
CPC .............. *A61B 2017/0445* (2013.01); *A61B 2017/0448* (2013.01); *A61B 2017/0453* (2013.01); *A61B 2017/0464* (2013.01)

(58) Field of Classification Search
CPC .... A61B 2017/0458; A61B 2017/0459; A61B 2017/0453
USPC ................................ 606/232, 301–304, 321
See application file for complete search history.

(56) References Cited

U.S. PATENT DOCUMENTS

| | | | |
|---|---|---|---|
| 3,268,965 A | | 8/1966 | Arthur |
| 4,636,121 A | | 1/1987 | Miller |
| 4,738,255 A | | 4/1988 | Goble et al. |
| 4,750,492 A | | 6/1988 | Jacobs |
| 4,870,957 A | | 10/1989 | Goble et al. |
| 4,927,421 A | | 5/1990 | Goble et al. |
| 5,037,422 A | | 8/1991 | Hayhurst et al. |
| 5,100,417 A | | 3/1992 | Cerier et al. |
| 5,102,421 A | | 4/1992 | Anspach, Jr. |
| 5,141,520 A | | 8/1992 | Goble et al. |
| 5,152,790 A | | 10/1992 | Rosenberg et al. |
| 5,156,616 A | | 10/1992 | Meadows et al. |
| 5,176,682 A | | 1/1993 | Chow |
| 5,258,016 A | | 11/1993 | DiPoto et al. |
| 5,268,001 A | | 12/1993 | Nicholson et al. |
| 5,356,435 A | | 10/1994 | Thein |
| 5,370,662 A | | 12/1994 | Stone et al. |
| 5,376,119 A | | 12/1994 | Zimmermann et al. |
| 5,383,905 A | | 1/1995 | Golds et al. |
| 5,423,860 A | | 6/1995 | Lizardi et al. |
| 5,458,601 A | | 10/1995 | Young et al. |
| 5,464,427 A | | 11/1995 | Curtis et al. |
| 5,480,403 A | | 1/1996 | Lee et al. |
| 5,486,197 A | | 1/1996 | Le et al. |
| 5,500,000 A | | 3/1996 | Feagin et al. |
| 5,505,735 A | | 4/1996 | Li |
| 5,522,843 A | | 6/1996 | Zang |
| 5,527,342 A | | 6/1996 | Pietrzak et al. |
| 5,545,180 A | | 8/1996 | Le et al. |
| 5,584,835 A | | 12/1996 | Greenfield |
| 5,584,860 A | | 12/1996 | Goble et al. |
| 5,607,432 A | | 3/1997 | Fucci |
| 5,630,824 A | | 5/1997 | Hart |
| 5,690,676 A | | 11/1997 | DiPoto et al. |
| 5,702,397 A | * | 12/1997 | Goble et al. ............ 606/232 |
| 5,707,395 A | | 1/1998 | Li |
| 5,720,765 A | | 2/1998 | Thal |
| 5,723,013 A | | 3/1998 | Jeanson et al. |
| 5,725,529 A | | 3/1998 | Nicholson et al. |
| 5,728,136 A | | 3/1998 | Thal |
| 5,733,307 A | | 3/1998 | Dinsdale |
| 5,797,963 A | | 8/1998 | McDevitt |
| 5,827,291 A | | 10/1998 | Fucci et al. |
| 5,849,004 A | * | 12/1998 | Bramlet ................... 606/232 |
| 5,911,721 A | | 6/1999 | Nicholson et al. |
| RE36,289 E | | 8/1999 | Le et al. |
| 5,935,129 A | | 8/1999 | McDevitt et al. |
| 5,948,000 A | | 9/1999 | Larsen et al. |
| 5,948,001 A | | 9/1999 | Larsen |
| 5,957,953 A | * | 9/1999 | DiPoto et al. ........... 606/232 |
| 6,010,525 A | * | 1/2000 | Bonutti et al. .......... 606/232 |
| 6,086,608 A | * | 7/2000 | Ek et al. ................. 606/232 |
| 6,117,162 A | | 9/2000 | Schmieding et al. |
| 6,129,763 A | | 10/2000 | Chauvin et al. |
| 6,136,032 A | | 10/2000 | Perice et al. |
| 6,146,387 A | | 11/2000 | Trott et al. |
| 6,149,669 A | | 11/2000 | Li |
| 6,152,934 A | | 11/2000 | Harper et al. |
| 6,159,235 A | | 12/2000 | Kim |
| 6,165,203 A | | 12/2000 | Krebs |
| 6,200,329 B1 | | 3/2001 | Fung et al. |
| 6,200,330 B1 | | 3/2001 | Benderev et al. |
| 6,206,886 B1 | | 3/2001 | Bennett |
| 6,214,007 B1 | | 4/2001 | Anderson |
| 6,228,096 B1 | | 5/2001 | Marchand |
| 6,267,766 B1 | | 7/2001 | Burkhart |
| 6,287,324 B1 | | 9/2001 | Yarnitsky et al. |
| 6,319,271 B1 | | 11/2001 | Schwartz et al. |
| 6,368,326 B1 | | 4/2002 | Dakin et al. |
| 6,436,124 B1 | | 8/2002 | Anderson et al. |
| 6,436,142 B1 | | 8/2002 | Paes et al. |
| RE37,963 E | | 1/2003 | Thal |
| 6,517,542 B1 | | 2/2003 | Papay et al. |
| 6,520,980 B1 | | 2/2003 | Foerster |
| 6,527,794 B1 | | 3/2003 | McDevitt et al. |
| 6,533,816 B2 | | 3/2003 | Sklar |
| 6,575,987 B2 | | 6/2003 | Gellman et al. |
| 6,585,730 B1 | | 7/2003 | Foerster |
| 6,616,694 B1 | | 9/2003 | Hart |
| 6,641,596 B1 | | 11/2003 | Lizardi |
| 6,652,563 B2 | | 11/2003 | Dreyfuss |
| 6,692,516 B2 | | 2/2004 | West et al. |
| 6,736,829 B1 | | 5/2004 | Li et al. |
| 6,783,527 B2 | | 8/2004 | Drewry et al. |
| 6,840,953 B2 | | 1/2005 | Martinek |
| 7,008,451 B2 | | 3/2006 | Justin et al. |
| 7,083,638 B2 | | 8/2006 | Foerster |
| 7,090,690 B2 | | 8/2006 | Foerster et al. |
| 7,329,272 B2 | | 2/2008 | Burkhart et al. |
| 7,416,556 B2 | | 8/2008 | Jackson |
| 7,491,217 B1 | * | 2/2009 | Hendren et al. ......... 606/232 |
| 7,517,357 B2 | | 4/2009 | Abrams et al. |
| 7,585,311 B2 | | 9/2009 | Green et al. |
| 7,604,640 B2 | | 10/2009 | Kana |
| 7,938,847 B2 | | 5/2011 | Fanton et al. |
| 8,118,835 B2 | | 2/2012 | Weisel et al. |
| 8,133,258 B2 | | 3/2012 | Foerster et al. |
| 8,137,381 B2 | | 3/2012 | Foerster et al. |
| 8,162,978 B2 | | 4/2012 | Lombardo et al. |
| 9,179,907 B2 | | 11/2015 | ElAttrache et al. |
| 9,345,467 B2 | * | 5/2016 | Lunn et al. ........ A61B 17/0401 |
| 2001/0007072 A1 | | 7/2001 | Steiner et al. |
| 2002/0013608 A1 | | 1/2002 | ElAttrache et al. |
| 2002/0058966 A1 | | 5/2002 | Tormala et al. |
| 2002/0147463 A1 | | 10/2002 | Martinek |
| 2002/0161401 A1 | | 10/2002 | Steiner |
| 2002/0188301 A1 | | 12/2002 | Dallara |
| 2003/0065361 A1 | | 4/2003 | Dreyfuss |
| 2003/0065390 A1 | | 4/2003 | Justin et al. |
| 2003/0083669 A1 | | 5/2003 | Gleason |
| 2003/0088272 A1 | | 5/2003 | Smith |
| 2003/0187446 A1 | | 10/2003 | Overaker et al. |
| 2003/0195563 A1 | | 10/2003 | Foerster |
| 2003/0208210 A1 | | 11/2003 | Dreyfuss et al. |
| 2004/0088004 A1 | | 5/2004 | Rosch |
| 2004/0093031 A1 | | 5/2004 | Burkhart et al. |
| 2004/0098050 A1 | | 5/2004 | Foerster et al. |
| 2004/0098052 A1 | | 5/2004 | West et al. |
| 2004/0133239 A1 | | 7/2004 | Singhatat |
| 2004/0138706 A1 | | 7/2004 | Abrams et al. |
| 2004/0138707 A1 | | 7/2004 | Greenhalgh |
| 2004/0225313 A1 | | 11/2004 | Kanner et al. |
| 2005/0033364 A1 | | 2/2005 | Gregoire et al. |
| 2005/0055052 A1 | | 3/2005 | Lombardo et al. |
| 2005/0107828 A1 | | 5/2005 | Reese |
| 2005/0216015 A1 | | 9/2005 | Kreidler |
| 2005/0222618 A1 | | 10/2005 | Dreyfuss et al. |
| 2005/0245932 A1 | * | 11/2005 | Fanton et al. ................ 606/72 |
| 2006/0004364 A1 | | 1/2006 | Green et al. |
| 2006/0058800 A1 | | 3/2006 | Ainsworth et al. |
| 2006/0079904 A1 | | 4/2006 | Thal |
| 2006/0235413 A1 | | 10/2006 | Denham et al. |
| 2006/0253119 A1 | | 11/2006 | Berberich et al. |

(56) References Cited

U.S. PATENT DOCUMENTS

| | | | |
|---|---|---|---|
| 2006/0271060 A1 | 11/2006 | Gordon | |
| 2006/0282081 A1 | 12/2006 | Fanton et al. | |
| 2007/0005068 A1 | 1/2007 | Sklar | |
| 2007/0005069 A1 | 1/2007 | Contiliano et al. | |
| 2007/0038219 A1 | 2/2007 | Matthis et al. | |
| 2007/0038221 A1* | 2/2007 | Fine et al. | A61F 2/0811 606/323 |
| 2007/0142835 A1 | 6/2007 | Green et al. | |
| 2007/0167950 A1 | 7/2007 | Tauro et al. | |
| 2007/0203498 A1 | 8/2007 | Gerber et al. | |
| 2007/0218424 A1 | 9/2007 | Vuorisalo et al. | |
| 2007/0225736 A1 | 9/2007 | Zeiner et al. | |
| 2007/0288023 A1 | 12/2007 | Pellegrino et al. | |
| 2008/0009904 A1 | 1/2008 | Bourque et al. | |
| 2008/0015594 A1 | 1/2008 | Ritchart et al. | |
| 2008/0033460 A1 | 2/2008 | Ziniti et al. | |
| 2008/0051836 A1 | 2/2008 | Foerster et al. | |
| 2008/0077161 A1 | 3/2008 | Kaplan | |
| 2008/0125815 A1 | 5/2008 | Heaven et al. | |
| 2008/0133007 A1* | 6/2008 | Donnelly et al. | 623/13.14 |
| 2008/0208253 A1 | 8/2008 | Dreyfuss et al. | |
| 2008/0215061 A1 | 9/2008 | Schumacher et al. | |
| 2008/0249567 A1 | 10/2008 | Kaplan | |
| 2008/0281353 A1 | 11/2008 | Aranyi et al. | |
| 2009/0112270 A1 | 4/2009 | Lunn et al. | |
| 2009/0228055 A1* | 9/2009 | Jackson | A61B 17/7091 606/86 A |
| 2009/0312794 A1* | 12/2009 | Nason et al. | 606/232 |
| 2009/0318965 A1 | 12/2009 | Burkhart | |
| 2009/0326545 A1 | 12/2009 | Schaffhausen | |
| 2010/0004683 A1* | 1/2010 | Hoof et al. | 606/232 |
| 2010/0094355 A1* | 4/2010 | Trenhaile | 606/304 |
| 2010/0318125 A1 | 12/2010 | Gerber et al. | |

FOREIGN PATENT DOCUMENTS

| | | |
|---|---|---|
| EP | 0611551 | 2/1994 |
| EP | 0673624 | 9/1995 |
| EP | 1486171 | 12/2004 |
| EP | 1491162 A2 | 12/2004 |
| EP | 1825817 | 2/2007 |
| EP | 1825817 A1 | 8/2007 |
| EP | 1884198 | 4/2008 |
| JP | H04-250155 | 7/1992 |
| JP | 11506644 | 6/1999 |
| JP | H11-511357 | 10/1999 |
| JP | 2000-505324 | 5/2000 |
| JP | 2001-505081 | 4/2001 |
| JP | 2003505128 | 2/2003 |
| JP | 2003528648 | 9/2003 |
| JP | 2006-501003 | 1/2006 |
| JP | 2007532269 | 11/2007 |
| WO | 9639082 | 12/1996 |
| WO | 9706731 | 2/1997 |
| WO | 97/07743 | 3/1997 |
| WO | 97/29693 | 8/1997 |
| WO | 9835606 | 8/1998 |
| WO | 0106909 | 2/2001 |
| WO | 0110312 | 5/2001 |
| WO | 02/32345 | 4/2002 |
| WO | WO0238059 A2 | 5/2002 |
| WO | 2004/062506 | 7/2004 |
| WO | 2004096080 | 11/2004 |
| WO | 2005020832 | 3/2005 |
| WO | 2005037055 | 4/2005 |
| WO | 2005/102790 | 11/2005 |
| WO | 2006/044491 | 4/2006 |
| WO | 2006060035 | 6/2006 |
| WO | WO2006067548 A1 | 6/2006 |
| WO | 2006/078864 | 7/2006 |
| WO | 2007134248 | 11/2007 |
| WO | 2008/011417 | 1/2008 |
| WO | WO2008054814 A2 | 5/2008 |
| WO | WO2009055800 A1 | 4/2009 |

OTHER PUBLICATIONS

Office Action received for corresponding JP Application No. 2010-531316, dated Feb. 26, 2013.
International Search Report and Written Opinion for PCT/US2008/081342, dated Feb. 26, 2009.
International Search Report and Written Opinion for PCT/US2010/056107, dated May 25, 2011.
Partial International Search Report and Written Opinion for PCT/US2010/056107 dated Feb. 23, 2011.
Office Action issued in corresponding Australian patent application No. 2008316604 dated Feb. 5, 2013.
Office Action for corresponding Japanese application No. 2012-538921 dated Jul. 22, 2014.
Office Action for corresponding Japanese application No. 2013-164031 dated Jul. 28, 2014.
Office Action for corresponding Chinese application No. 201080061088.8 dated Jun. 23, 2014.
Office action received in corresponding European patent application No. 08 842 610.1-654 dated Feb. 11, 2015.
Office action received in corresponding Russian patent application No. 2012122617/14(034396) dated Feb. 19, 2015.
Office action received in corresponding Japanese patent application No. 2013-164031 dated Feb. 18, 2015.
Office action received in corresponding Chinese patent application No. 201080061088.8 dated Feb. 27, 2015.
Office action received in corresponding Japanese patent application No. 2012-538921 dated Mar. 26, 2015.
Office action received in corresponding Japanese patent application No. 2012-538921 dated Nov. 30, 2015.
Office action received in corresponding European patent application No. 08 842 610.1-1654 dated Sep. 23, 2015.
Office action received in corresponding Australian patent application No. 2010319635 dated Jan. 11, 2016.
Office action received in corresponding Australian patent application No. 2010319635 dated Apr. 29, 2015.
Office action received in corresponding European patent application No. 088426101.1-1654 dated Nov. 23, 2015.

\* cited by examiner

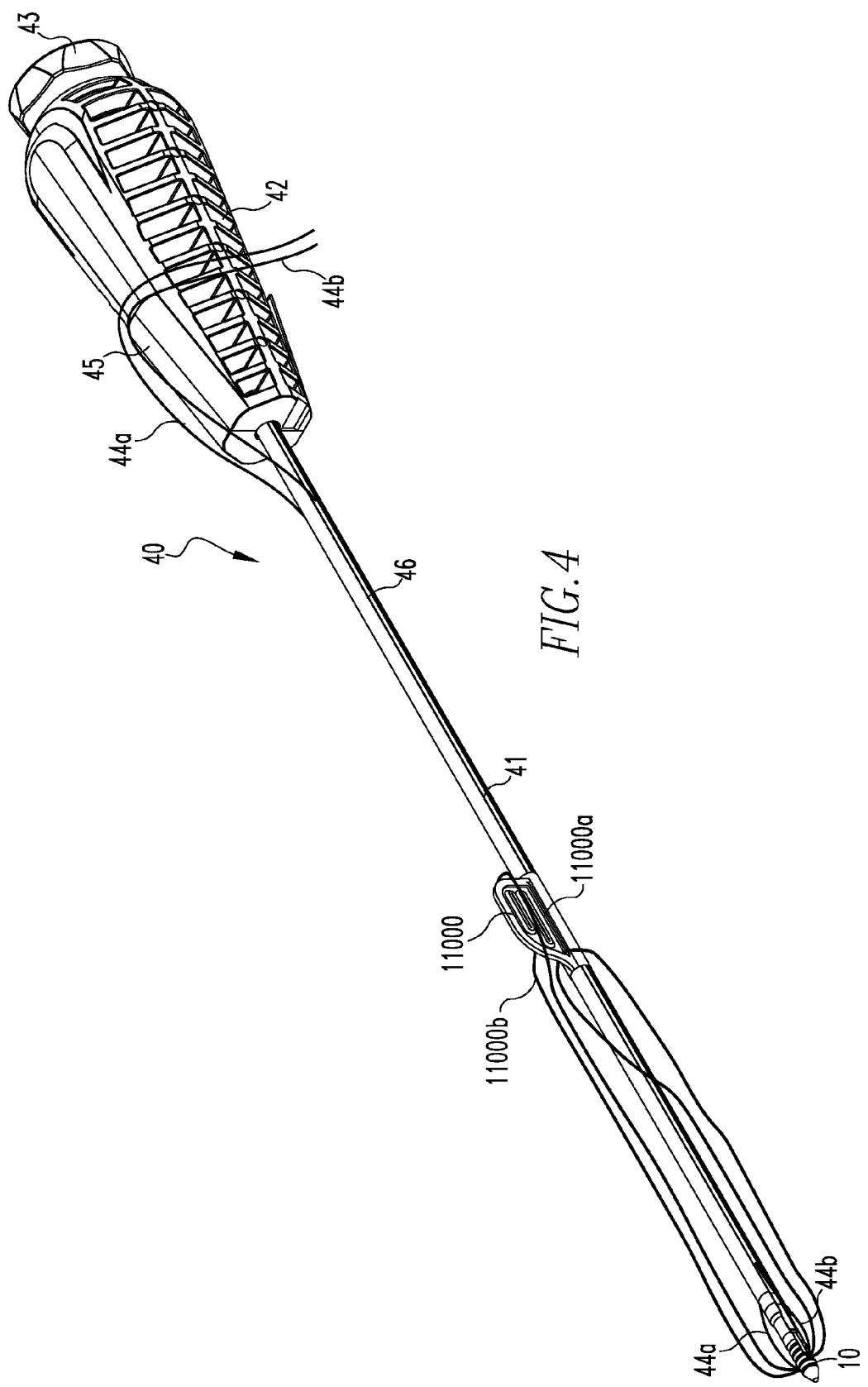

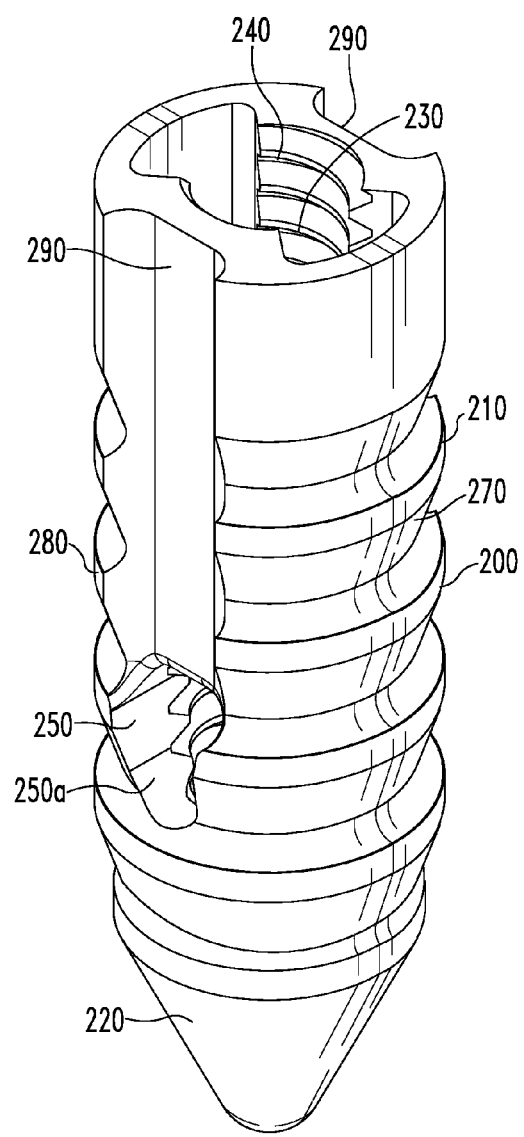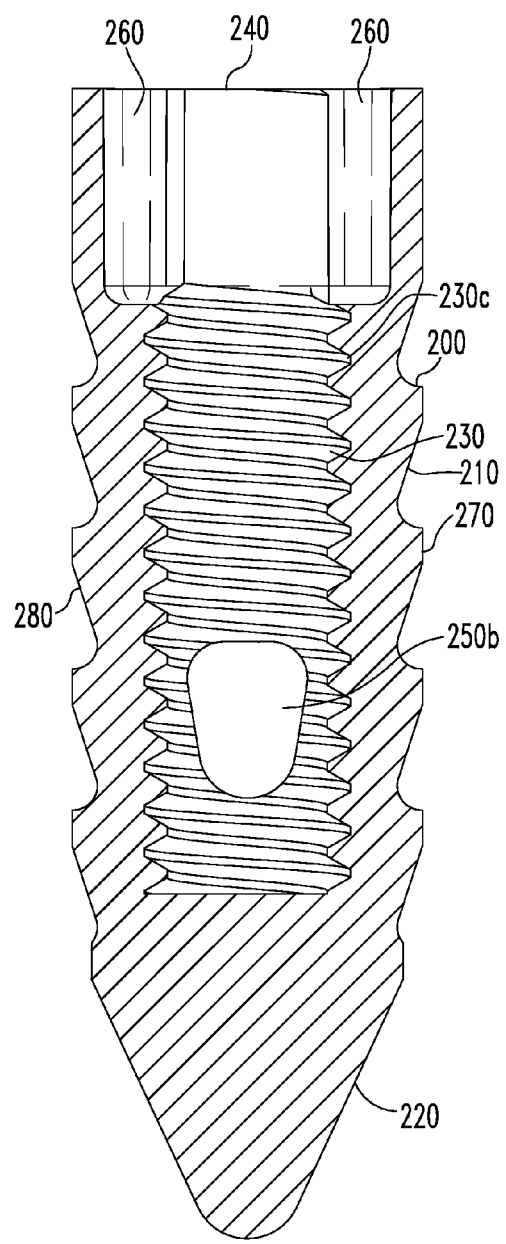
FIG.9
FIG.10

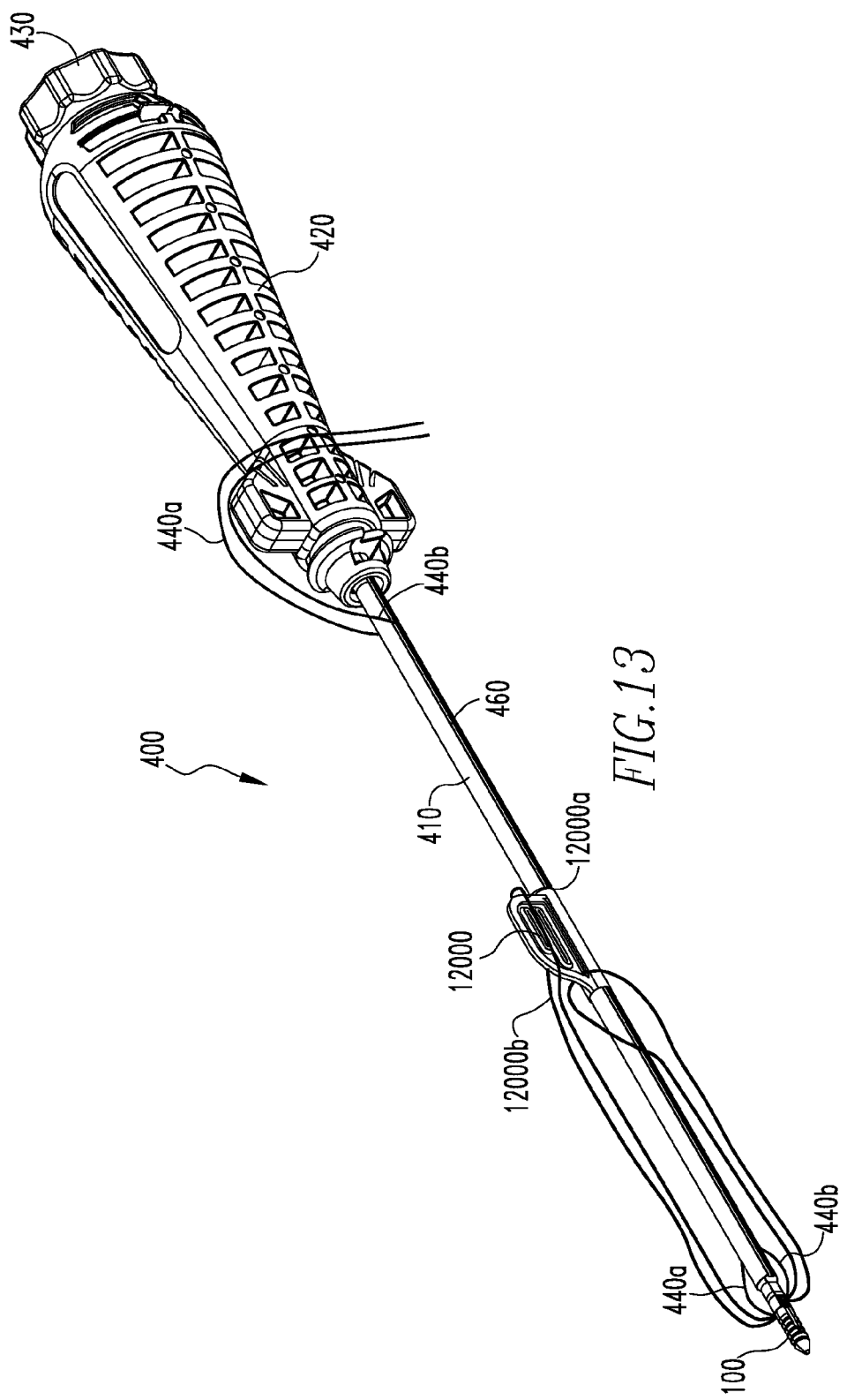

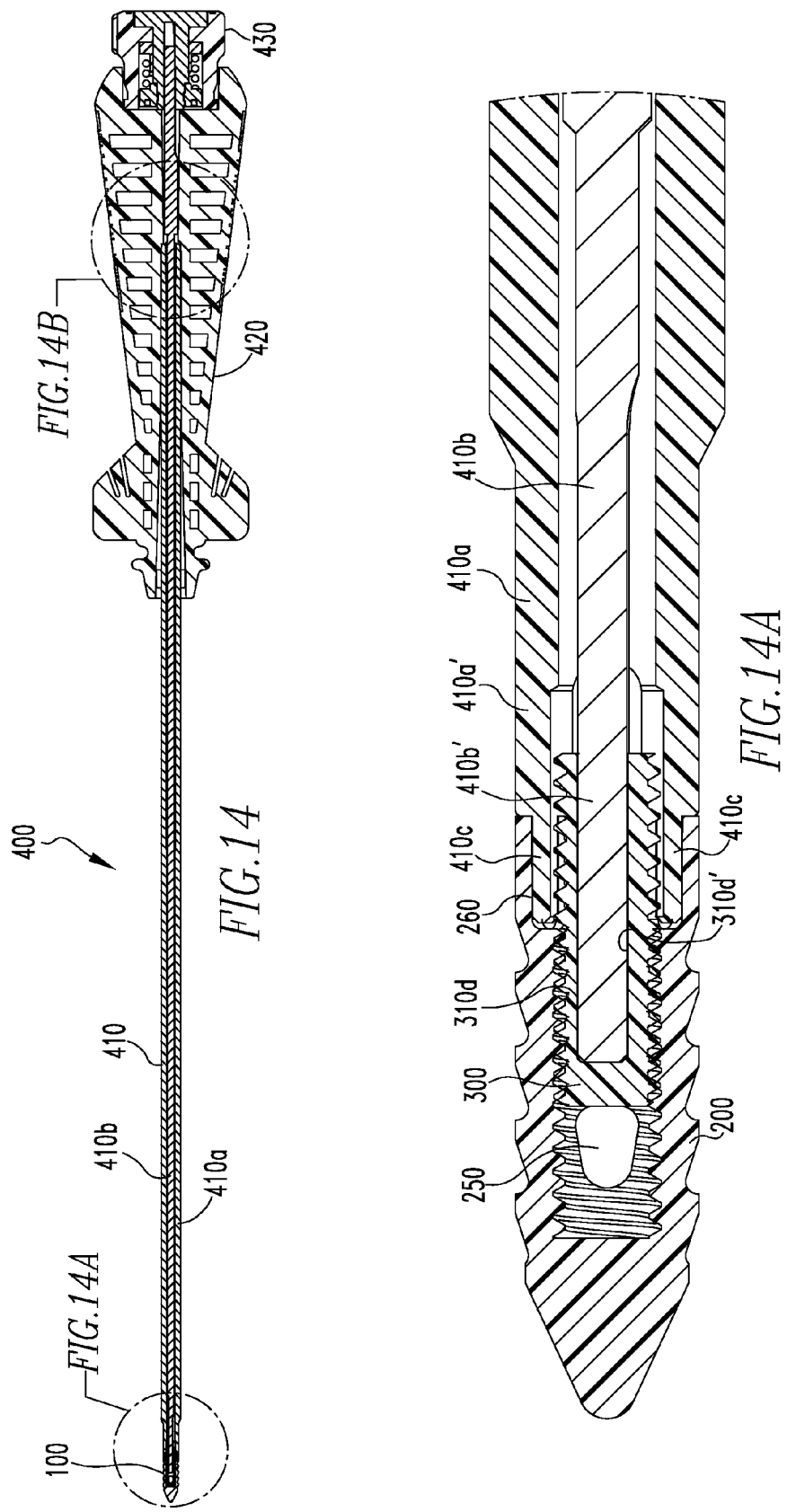

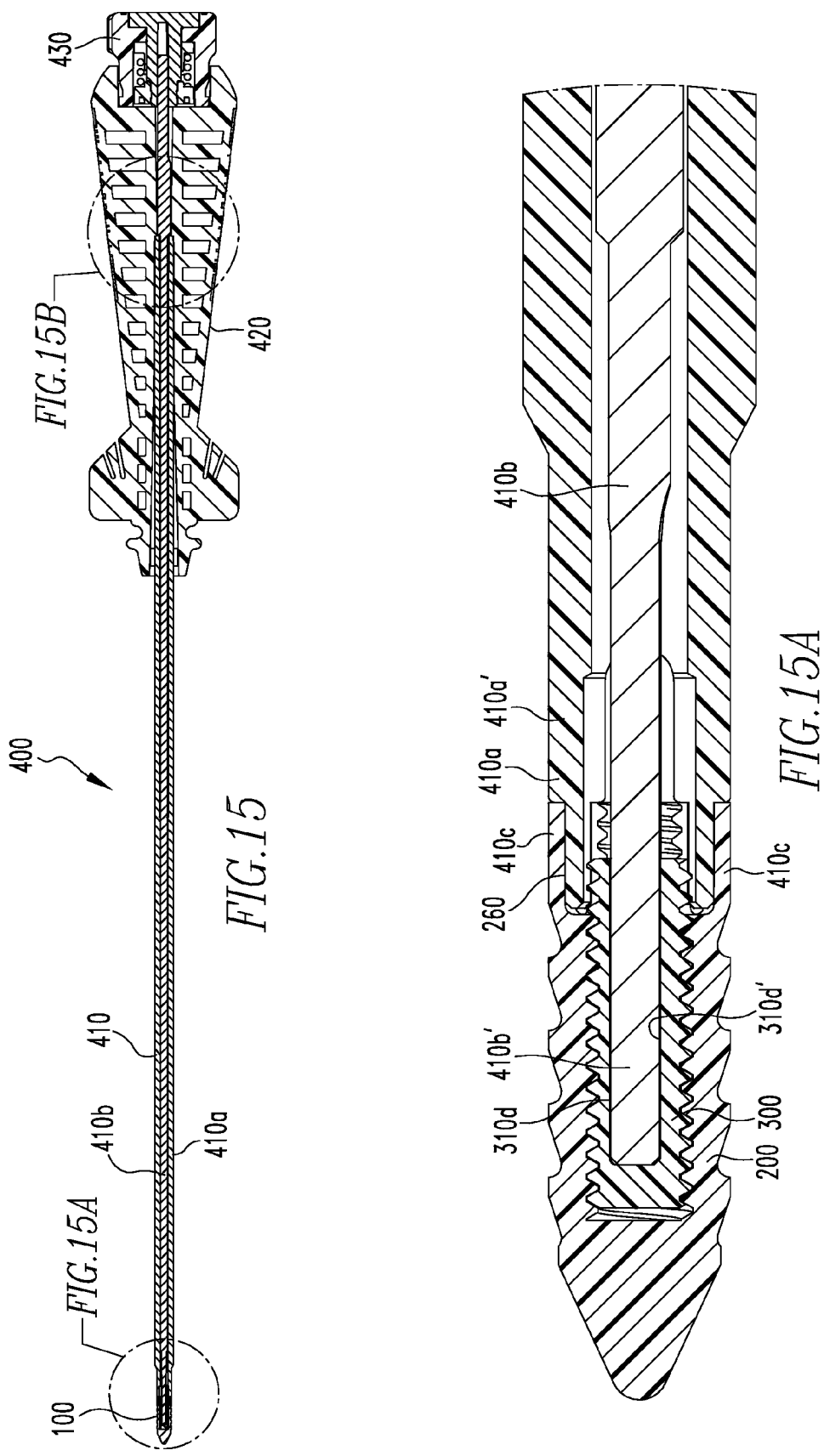

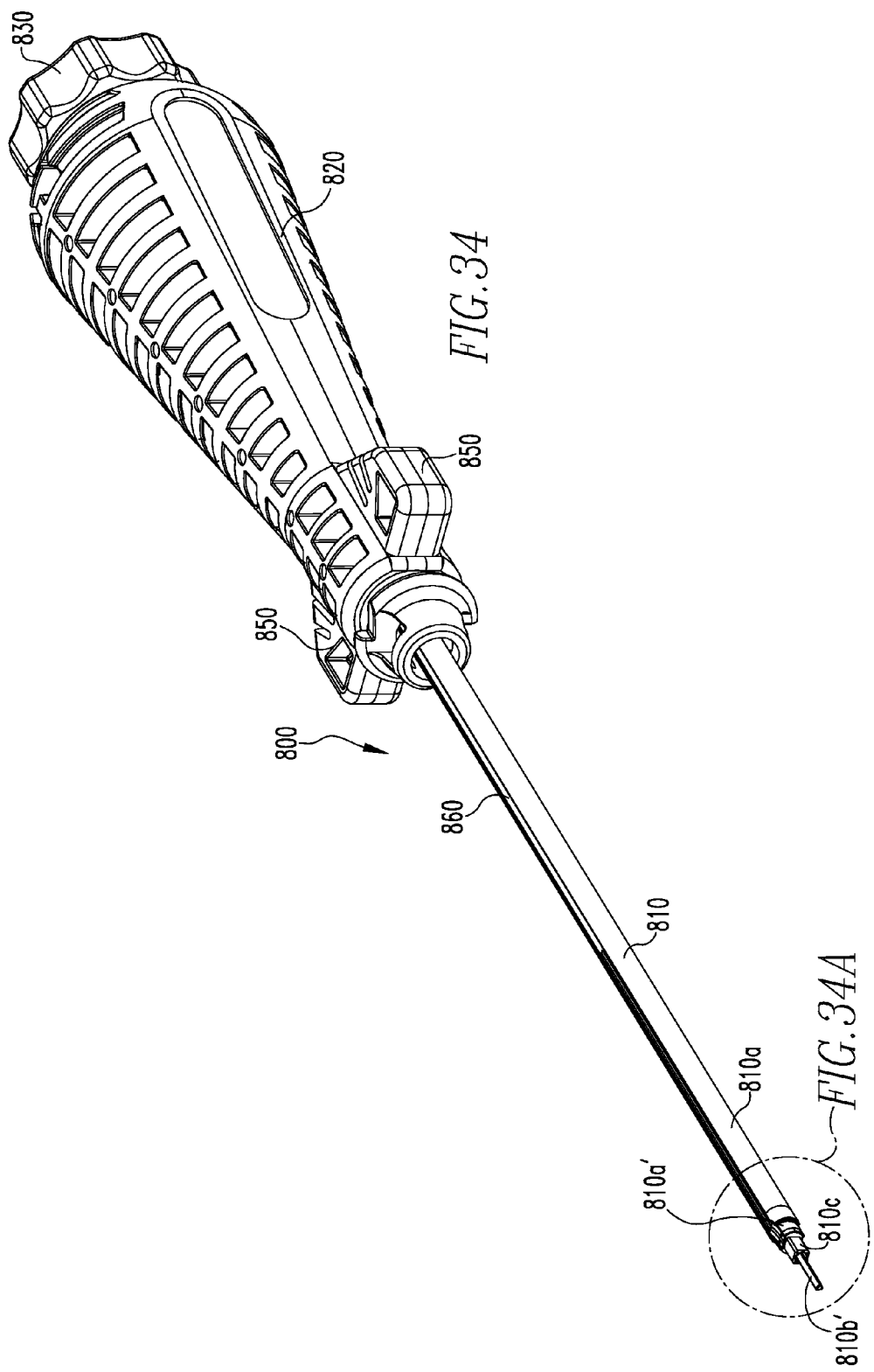

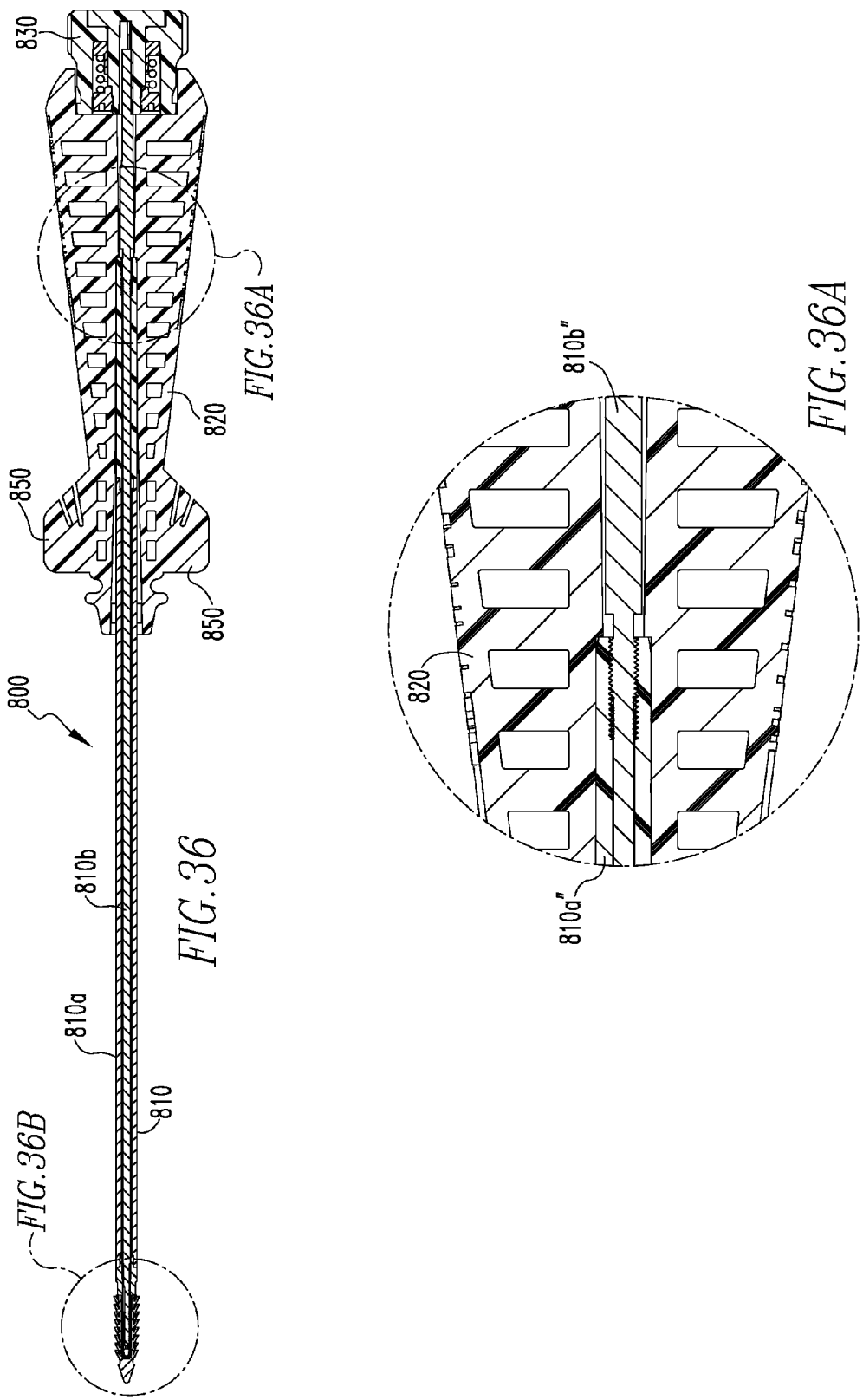

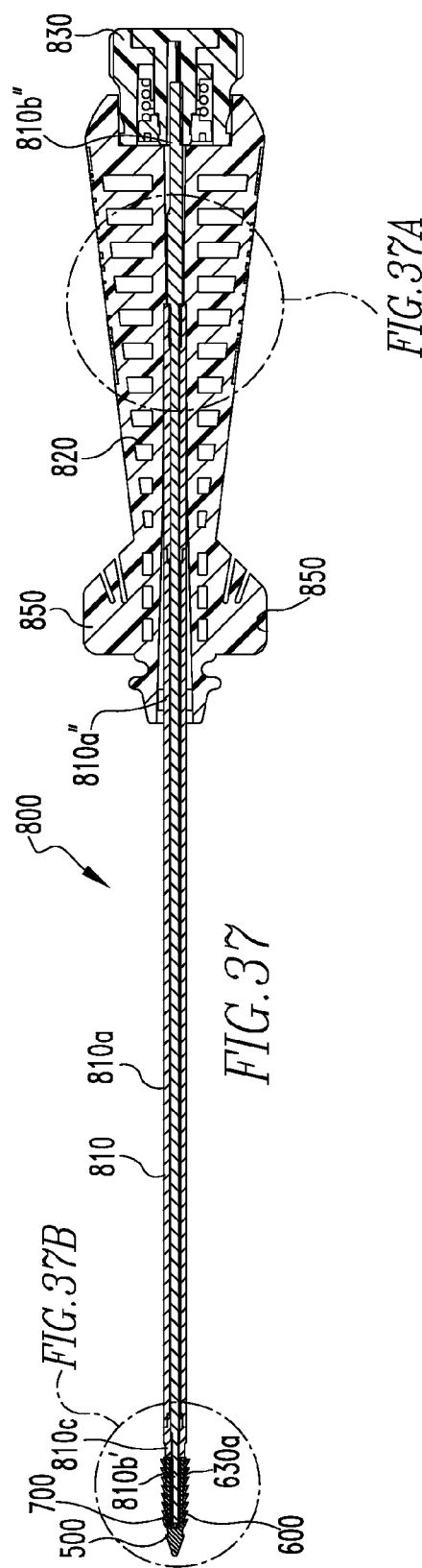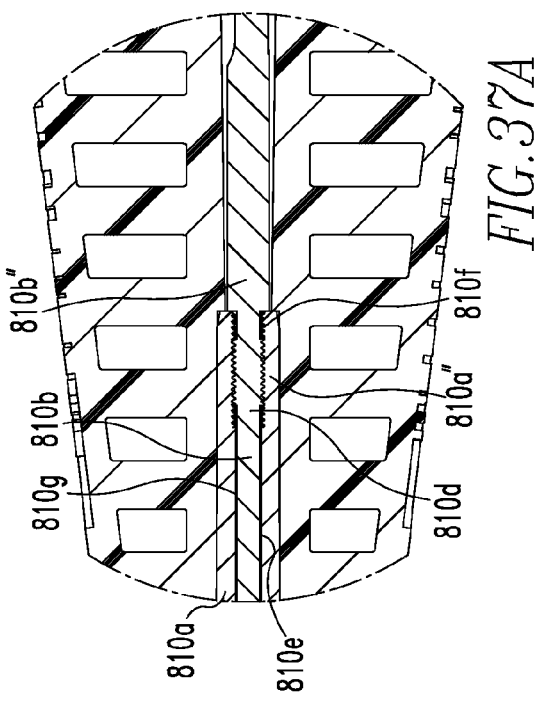

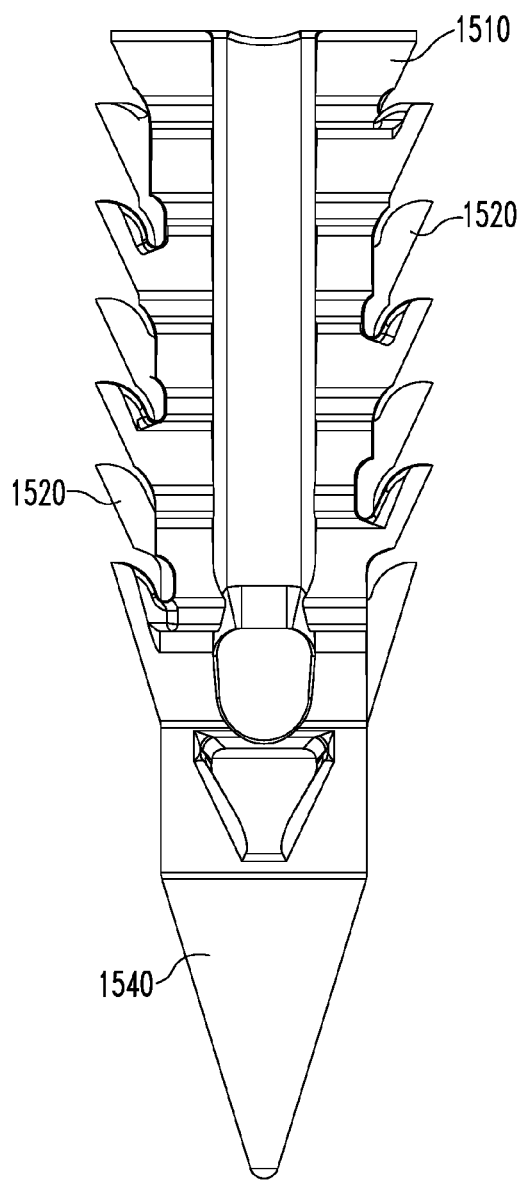
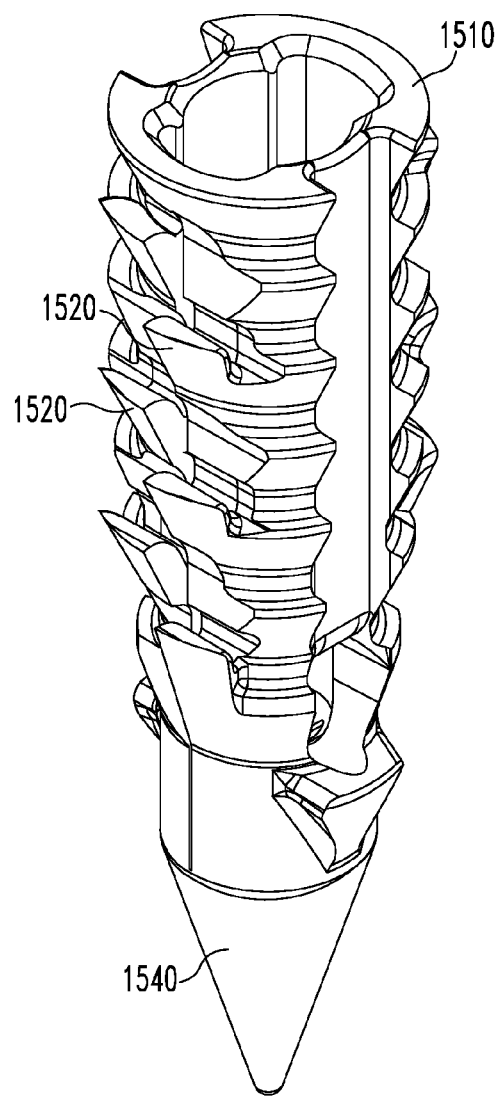
FIG.49
FIG.50

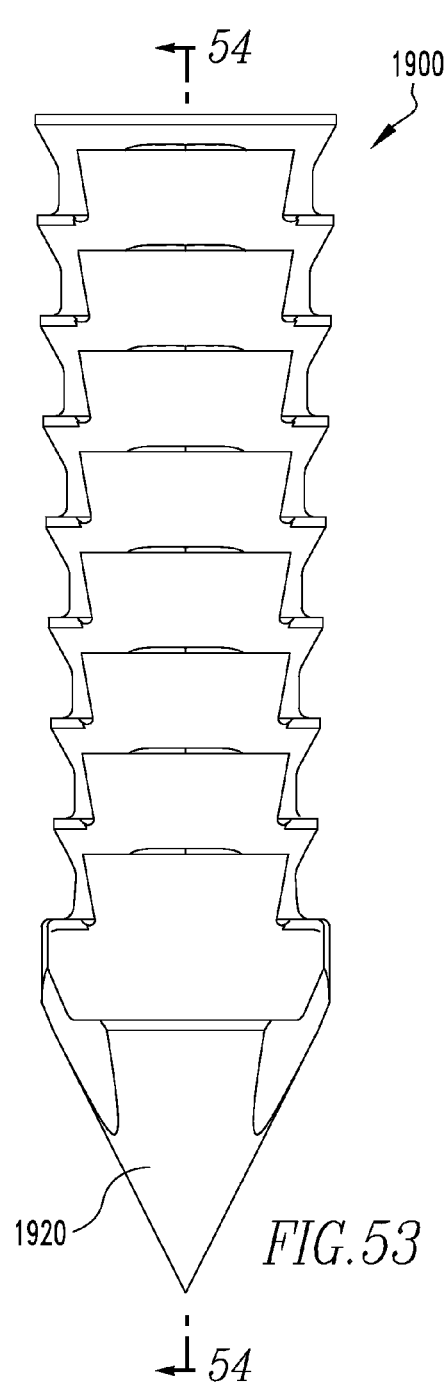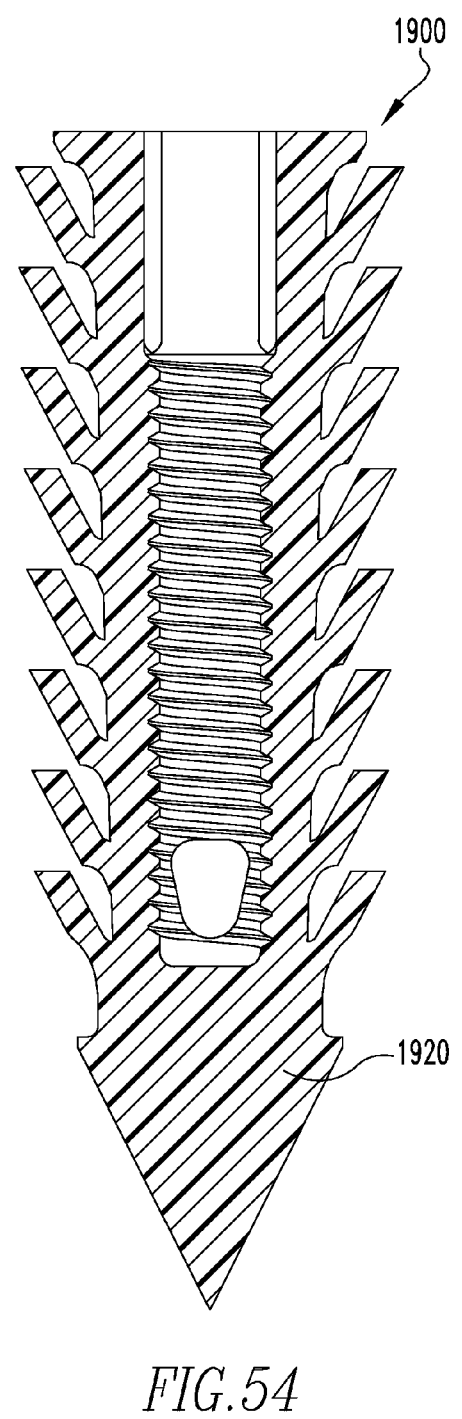
FIG.53
FIG.54

TISSUE REPAIR DEVICES

CROSS REFERENCE TO RELATED APPLICATIONS

This application claims priority to U.S. Patent Application No. 61/259,737, filed Nov. 10, 2009, U.S. Patent Application No. 61/259,739, filed Nov. 10, 2009, U.S. Patent Application No. 61/290,695, filed Dec. 29, 2009, U.S. Patent Application No. 61/312,481, filed Mar. 10, 2010, and U.S. Patent Application No. 61/334,221, filed May 13, 2010, the disclosures of which are incorporated herein by reference in their entireties.

BACKGROUND

Field of Technology

The present disclosure relates to tissue repair devices, and more specifically, to anchors, anchor assemblies, and delivery devices for use in securing tissue to bone.

Related Art

Arthroscopic procedures often require soft tissue to be reattached to bone. To achieve this, anchors are placed in the bone and sutures attached to the anchor are passed through the tissue to securely retain the tissue in place. A procedure and components for use in such procedure, that securely attaches tissue to bone, is needed. Such procedure must be able to be done in a quick and efficient manner with a minimum of recovery time for the patient.

SUMMARY

In an aspect, the present disclosure relates to an anchor assembly. The anchor assembly includes an anchor defining a cavity and an opening to the cavity; and a headless insertion member configured for arrangement within the anchor cavity, the insertion member including a body having a threaded proximal portion, a non-threaded distal portion, and a cannulation extending a partial length of the insertion member. In an embodiment, the cannulation is triangular shaped. In another embodiment, the anchor cavity includes a threaded proximal portion and a non-threaded distal portion. In yet another embodiment, the distal portion of the insertion member includes two segments and a tapered portion located between the segments.

In another aspect, the present disclosure relates to an anchor assembly. The anchor assembly includes an anchor defining a cavity and an opening to the cavity and a headless insertion member configured for arrangement within the anchor cavity, the insertion member including a fully threaded body and a cannulation extending a partial length of the insertion member.

In yet another aspect, the present disclosure relates to a surgical device. The surgical device includes a shaft including an outer member and an inner member slidably received within the outer member, the outer member including an inner surface having threads and the inner member including an outer surface having threads; a handle coupled to the shaft; and a knob coupled to the inner member, wherein the threads of the inner member and the threads of the outer member are engaged to allow for coupling of the inner member and the outer member and movement of the outer member relative to the inner member upon rotation of the knob. In an embodiment, the inner member is triangular-shaped. In another embodiment, the inner member includes a depth stop. In yet another embodiment, the outer member includes a tip extending from an end of the outer member. In a further embodiment, the tip is square-shaped.

In a further aspect, the present disclosure relates to an anchor assembly. The anchor assembly including an anchor defining a cavity and an opening to the cavity, the cavity including a non-threaded proximal portion and a threaded distal portion; and a headless insertion member configured for arrangement within the anchor cavity, the insertion member including a body and a cannulation extending a partial length of the insertion member, the body including a threaded proximal portion and a non-threaded distal portion. In an embodiment, the proximal portion is square-shaped.

In yet a further aspect, the present disclosure relates to an anchor. The anchor includes a body defining a cavity and an opening to the cavity, the body including an outer surface and channels extending from the outer surface to the cavity. In an embodiment, the body includes barbs, the channels located between the barbs. In another embodiment, the outer surface includes slots, the slots intersecting the barbs.

In an aspect, the present disclosure relates to an anchor assembly. The anchor assembly including an anchor defining a cavity and an opening to the cavity, the anchor including a body having an outer surface and barbs extending from the body and alternating in direction along the length of the body; and a headless insertion member configured for arrangement within the anchor cavity, the insertion member including a body and a cannulation extending a partial length of the insertion member.

In another aspect, the present disclosure relates to an anchor assembly. The anchor assembly includes an anchor including an outer body and an inner body coupled to the outer body, the outer body including a first feature and a second feature, the inner body including a first feature and a second feature, the first feature of the inner body and the first feature of the outer body engaged to allow for non-rotation of the inner body relative to the outer body and the second feature of the inner body and the second feature of the outer body engaged to allow for non-movement of the inner body relative to the outer body in an axial direction; and a headless insertion member configured for arrangement within the inner body, the insertion member including a body and a cannulation extending a partial length of the insertion member.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 4 shows an isometric view of the delivery device of the present disclosure.

FIG. 9 shows a side elevational view of the anchor of the anchor assembly of FIG. 8.

FIG. 10 shows a cross-sectional view of the anchor of FIG. 9.

FIG. 13 shows an isometric view of the delivery device for use with the anchor assembly of FIG. 8.

FIG. 14 shows a cross-sectional view of the delivery device and anchor assembly of FIG. 13 prior to use of the device and assembly during surgery.

FIG. 14A shows an exploded view of the distal end of the delivery device and the anchor assembly of FIG. 14.

FIG. 15 shows a cross-sectional view of the delivery device and anchor assembly of FIG. 13 after use of the device and assembly during surgery.

FIG. 15A shows an exploded view of the distal end of the delivery device and the anchor assembly of FIG. 15.

FIG. 34 shows an isometric view of the delivery device for use with the anchor assembly of FIG. 28.

FIG. 36 shows a cross-sectional view of the delivery device and anchor assembly of FIG. 35 prior to use of the device and assembly during surgery.

FIG. 36A shows an exploded view of the proximal ends of the outer and inner members of the delivery device of FIG. 36.

FIG. 37 shows a cross-sectional view of the delivery device and anchor assembly of FIG. 35 after to use of the device and assembly during surgery.

FIG. 37A shows an exploded view of the proximal ends of the outer and inner members of the delivery device of FIG. 37.

FIG. 49 shows a side view of a sixth embodiment of the anchor assembly of the present disclosure.

FIG. 50 shows a side elevational view of the anchor assembly of FIG. 49.

FIG. 53 shows a side view of an eighth embodiment of the anchor assembly of the present disclosure.

FIG. 54 shows a cross-sectional view of the anchor assembly of FIG. 53.

DETAILED DESCRIPTION OF THE EMBODIMENTS

The following description of the preferred embodiment(s) is merely exemplary in nature and is in no way intended to limit the disclosure, its application, or uses.

Figure 1:
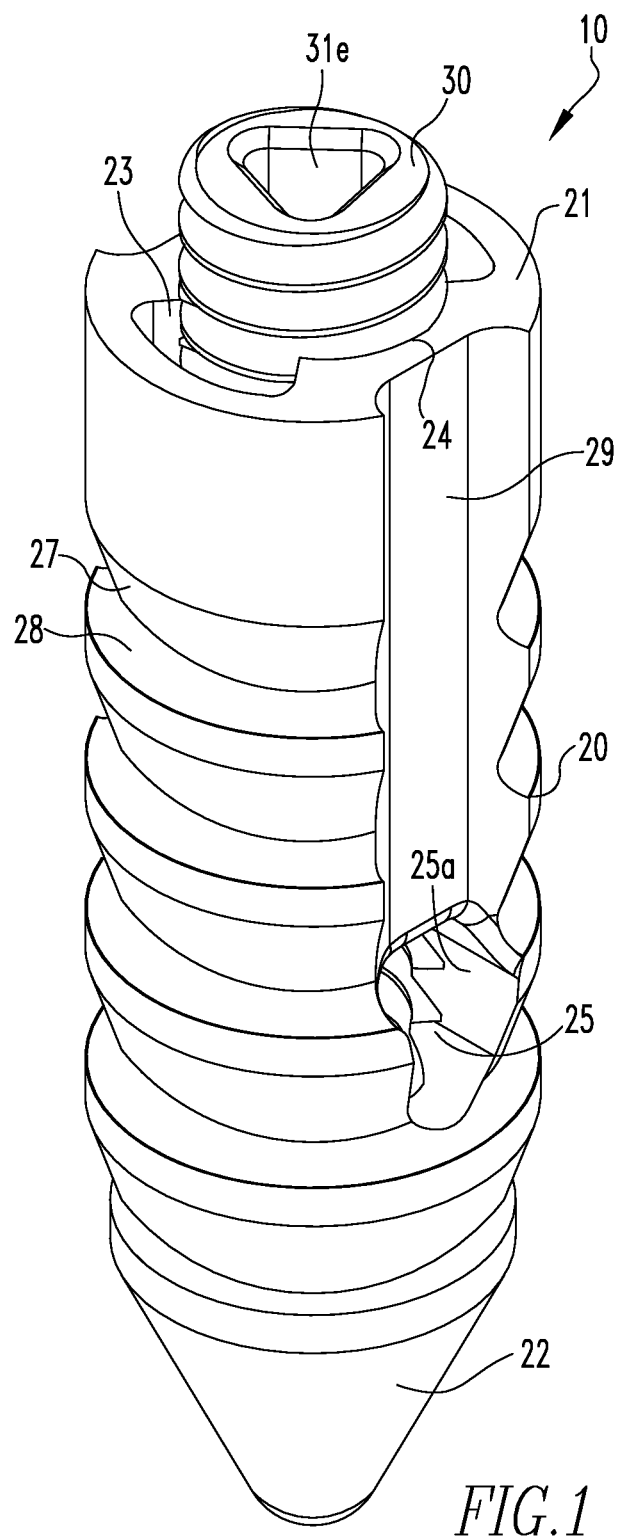
FIG. 1 shows a side elevational view of a first embodiment of the anchor assembly of the present disclosure.
Figure 2A:
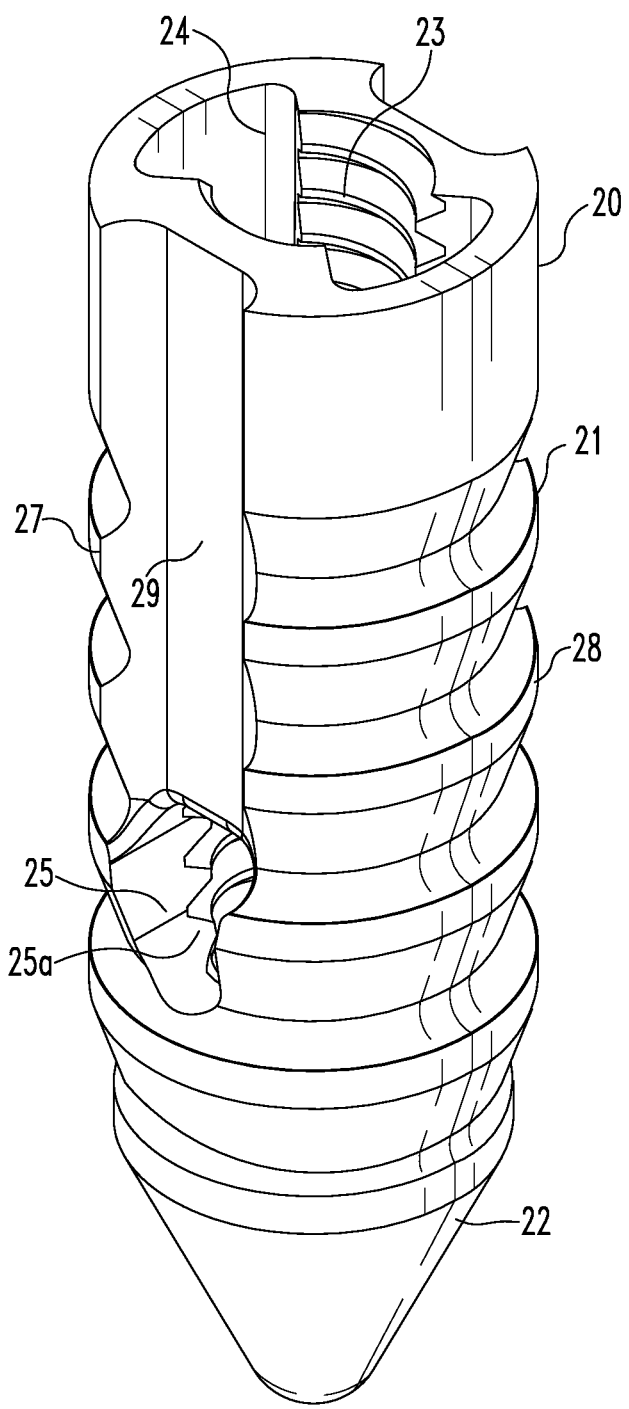
FIG. 2A shows a side elevational view of the anchor of the anchor assembly of FIG. 1.
Figure 2B:
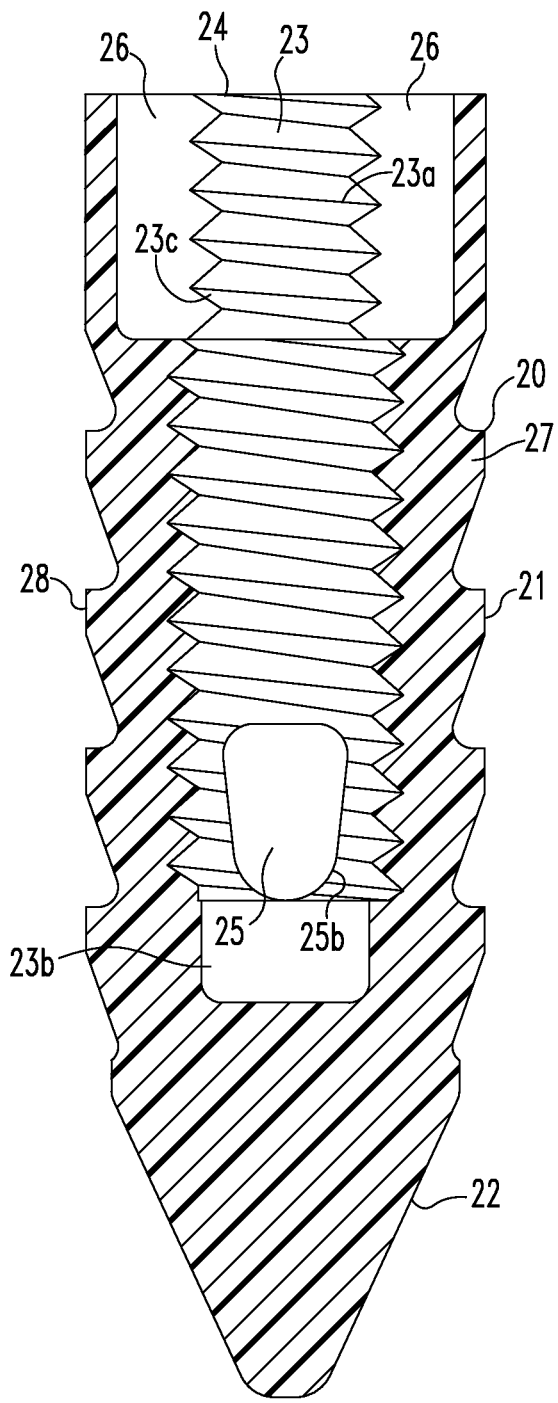
FIG. 2B shows a cross-sectional view of the anchor of FIG. 2A.

FIGS. 1, 2A-2B, and 3A-3B show a first embodiment of the anchor assembly 10 of the present disclosure and its components. The assembly 10 includes the anchor 20 and the insertion member 30. The anchor 20 includes a proximal portion 21, a distal portion 22, and an inner cavity 23. An opening 24 to the cavity 23 is located at the proximal portion 21 of the anchor 20. The anchor 20 also includes a transverse hole 25 extending through the anchor 20. The through hole 25 is for housing of a flexible member, such as suture. Openings 25a,b are located at each end of the through hole 25. The outer surface 27 of the proximal portion 21 also includes barbs 28 for substantially reducing the possibility of removal of the anchor 20 when inserted into bone. The outer surface 27 also includes at least two slots 29 extending from the openings 25a,b of the through hole 25. The slots 29 intersect the barbs 28 and are configured for housing of the suture after positioning of the anchor 20 in bone. As shown in FIG. 2B, the cavity 23 extends into and beyond the through hole 25 and includes a threaded proximal portion 23a and a non-threaded distal portion 23b. Also shown in FIG. 2B are a pair of depressions 26, each of which is located adjacent to the cavity 23. The depressions 26 are for housing of a delivery device, as will be further explained later.

Figure 3A:
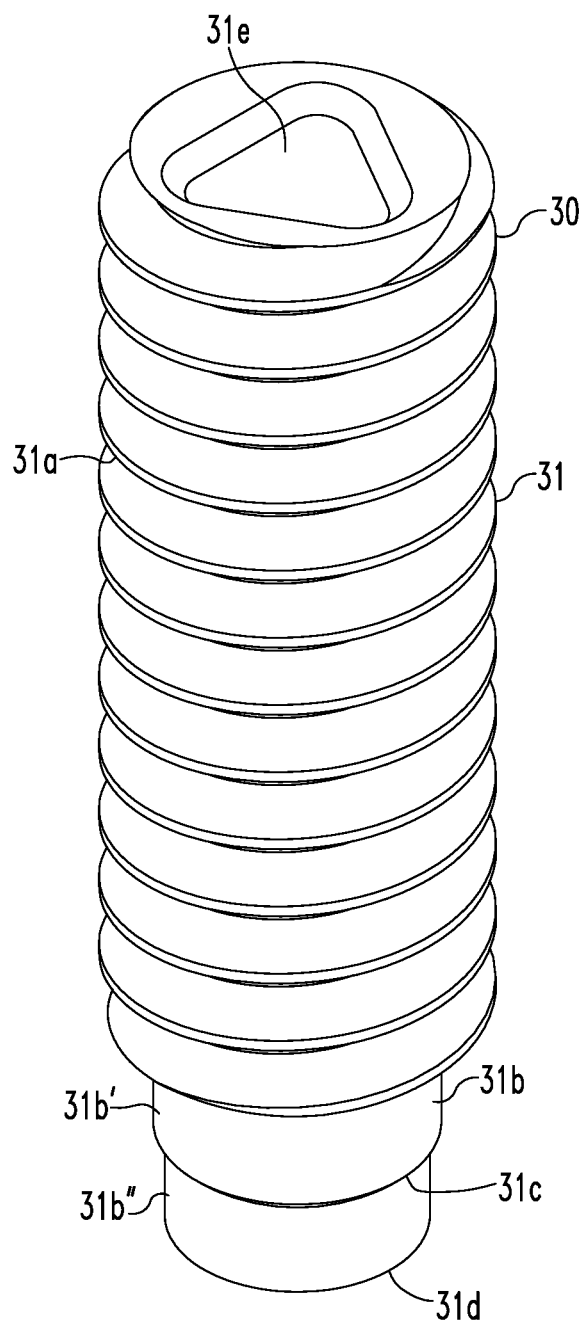
FIG. 3A shows a side elevational view of the insertion member of the anchor assembly of FIG. 1.
Figure 3B:
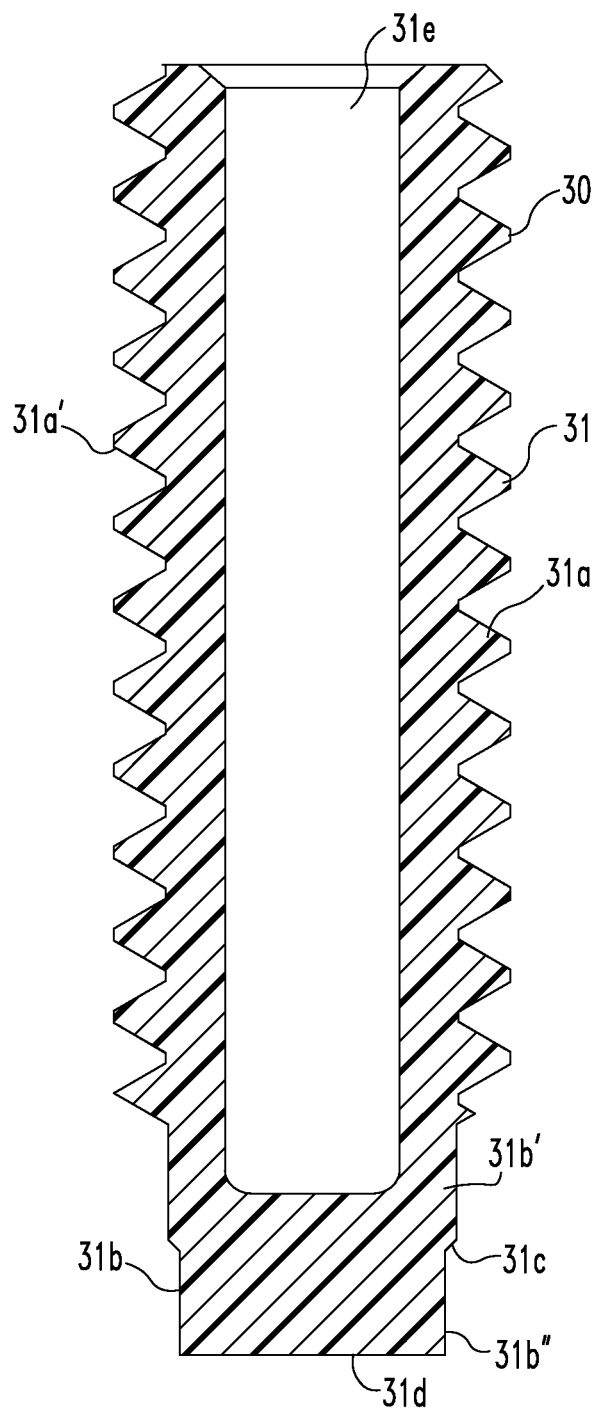
FIG. 3B shows a cross-sectional view of the insertion member of FIG. 3A.

The insertion member 30 includes a headless body 31 having a threaded proximal portion 31a and a non-threaded distal portion 31b. The distal portion 31b includes two segments 31b', 31b" and a tapered portion 31c located between the segments 31b', 31b". Segment 31b" has a flat end portion 31d. As shown in FIGS. 3A and 3B, the member 30 includes a triangular-shaped cannulation 31e that extends a partial length of the member 30. The threads 31a' are configured for engagement with the threads 23c of the cavity 23 when the insertion member 30 is arranged within the cavity 23, as will be further explained below.

FIGS. 4-7 show the delivery device 40 of the present disclosure. The device 40 includes a shaft 41, a handle 42 coupled to the shaft 41, and a knob 43 coupled to the handle 42. The shaft 41 includes an outer member 41a and an inner member 41b slidably disposed within and coupled to the outer member 41a. The inner member 41b includes a distal end 41b' configured for disposal within the cannulation 31e of the insertion member 30 and a proximal end 41b" coupled to the knob 43. The end 41b' is of a diameter such that it engages the wall 31e' of the cannulation 31e, thereby allowing movement of the member 30 when the knob 43 is rotated, as will be further described below. The outer member 41a includes prongs 41c located at a distal end 41a' of the outer member 41a and a proximal end 41a" coupled to the handle 42.

Prior to use, suture 44 is disposed within the through hole 25 and ends 44a,44b of the suture 44 are fixed to suture holders 45 located on handle 42. The suture 44 helps to keep anchor 20 coupled to the shaft 41. The delivery device 40 and its components, especially the handle 42 and knob 43, is similar to the delivery device shown and described in US Patent Application Publication 20100016869, the disclosure of which is incorporated herein by reference in its entirety. The ends 44a,44b of the suture 44 are also housed within channels 46 that extend along the shaft 41. A suture threader 11000 is also releasably coupled to the shaft 41. Threader 11000 includes a clip 11000a and a loop of suture 11000b coupled to the clip 11000a. Suture loop 11000b is disposed within the through hole 25 and placed around the clip 11000a.

Figure 5:
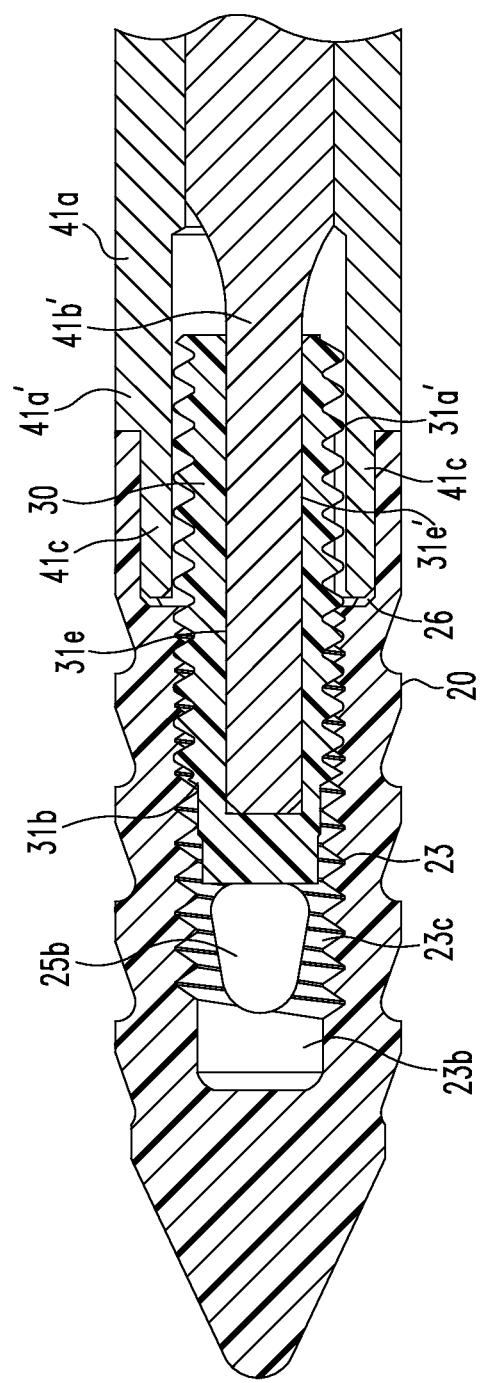
FIG. 5 shows a cross-sectional view of the distal ends of the outer and inner members of the delivery device of FIG. 4 and the anchor assembly of FIG. 1 prior to fixation of suture.
Figure 6:
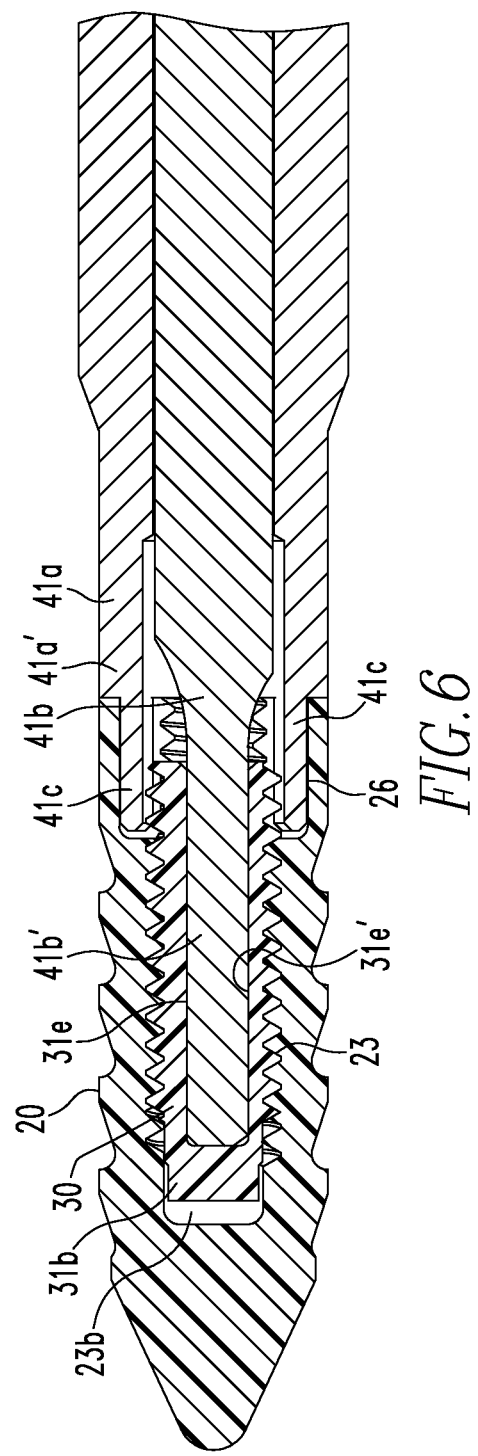
FIG. 6 shows a cross-sectional view of the distal ends of the outer and inner members of the delivery device of FIG. 4 and the anchor assembly of FIG. 1 after fixation of suture.

As shown in FIG. 5, the prongs 41c are disposed within the depressions 26. Once the anchor assembly 10 is disposed within bone, the prongs 41e help to hold the anchor 20 stationary while the insertion member 30 is moved relative to the anchor 20 via rotation of the knob 43. As will be further described below, FIG. 5 shows the location of the insertion member 30 prior to fixation of suture within the cavity 23, while FIG. 6 shows the location of the insertion member 30 after fixation of suture within the cavity 23. The non-threaded distal portion 31b is configured to be housed within the non-threaded distal portion 23b of the anchor 20.

Figure 7:
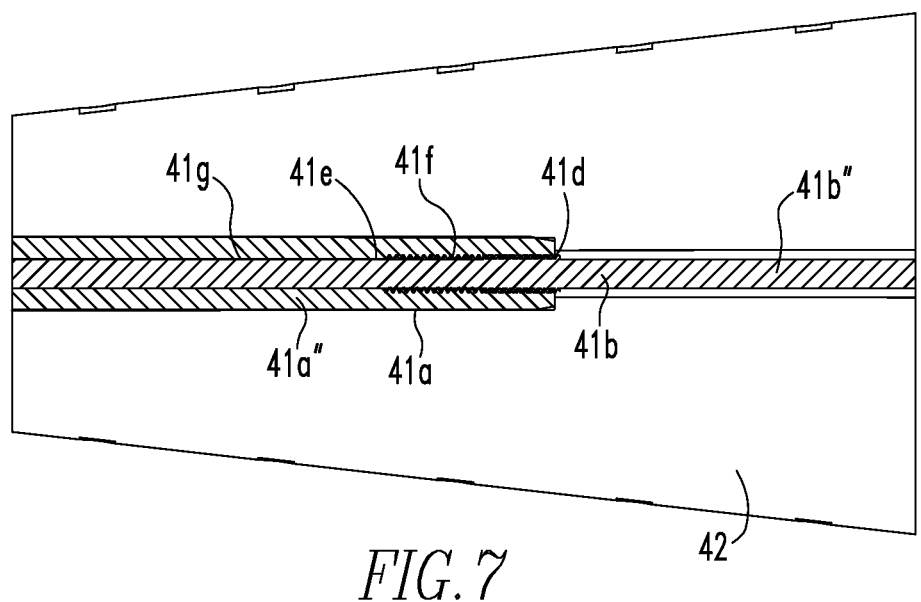
FIG. 7 shows a cross-sectional view of the proximal ends of the outer and inner members of the delivery device of FIG. 4.

Additionally, as shown in FIG. 7, the proximal end 41b" of the inner member 41b includes threads 41d on an outer surface 41e of the inner member 41b and the proximal end 41a" of the outer member 41a includes threads 41f on an inner surface 41g of the outer member 41a. Threads 41f engage threads 41d to allow for coupling of the outer and inner members 41a, 41b and axial movement of the inner member 41b relative to the outer member 41a, via rotation of the knob 43. Axial movement of the inner member 41b relative to the outer member 41a allows for axial movement of the insertion member 30 to the two locations shown in FIGS. 5 and 6.

FIGS. 8-12 show a second embodiment of the anchor assembly 100 of the present disclosure and its components. The assembly 100 includes the anchor 200 and the insertion member 300. The anchor 200 includes a proximal portion 210, a distal portion 220, and an inner cavity 230. An opening 240 to the cavity 230 is located at the proximal portion 210 of the anchor 200. The anchor 200 also includes a transverse hole 250 extending through the anchor 200. The through hole 250 is for housing of a flexible member, such as suture. Openings 250a,b are located at each end of the through hole 250. The outer surface 270 of the proximal portion 210 also includes barbs 280 for substantially reducing the possibility of removal of the anchor 200 when inserted into bone. The outer surface 270 also includes at least two slots 290 extending from the openings 250a,b of the through hole 250. The slots 290 intersect the barbs 280 and are configured for housing of the suture after positioning of the anchor 200 in bone. As shown in FIG. 10, the cavity 230 extends into and beyond the through hole 250. Also shown in FIG. 10 are a pair of depressions 260, each of which is located adjacent to the cavity 230. The depressions 260 are for housing of a delivery device, as will be further explained later.

Figure 8:
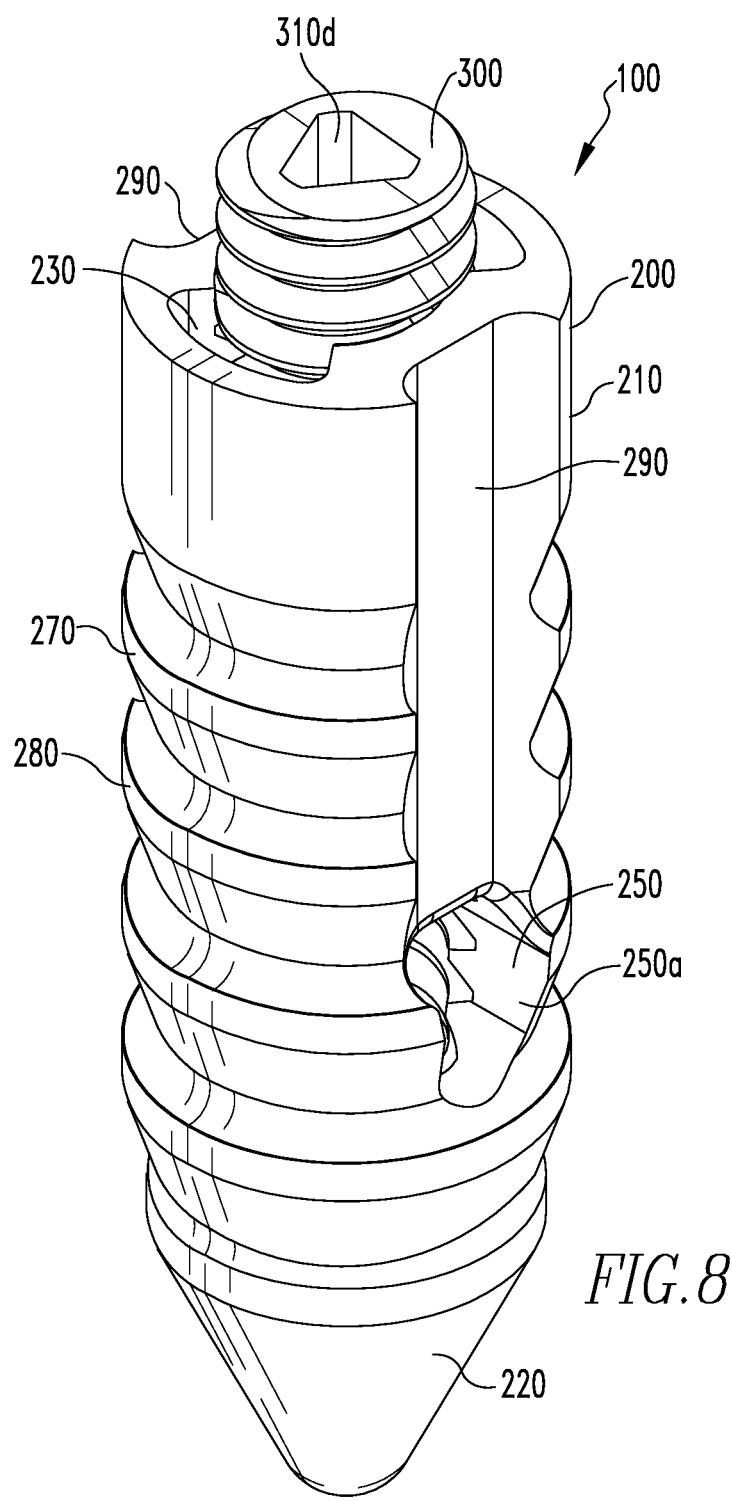
FIG. 8 shows a side elevational view of a second embodiment of the anchor assembly of the present disclosure.
Figure 11:
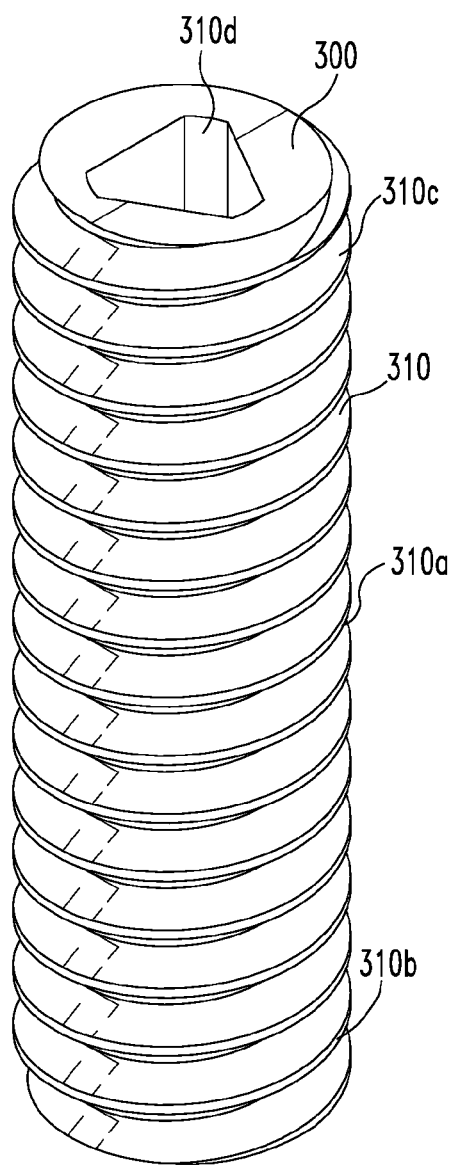
FIG. 11 shows a side elevational view of the insertion member of the anchor assembly FIG. 8.
Figure 12:
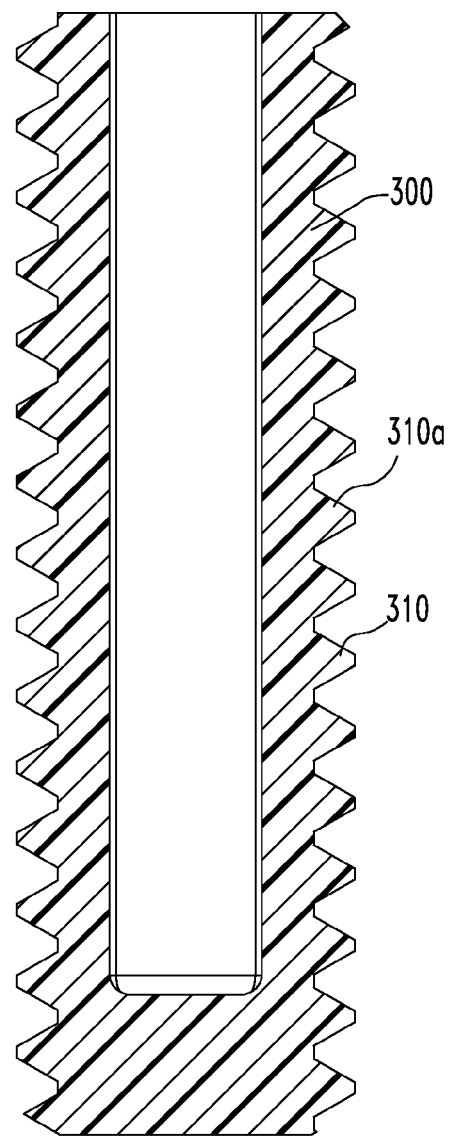
FIG. 12 shows a cross-sectional view of the insertion member of FIG. 11.

The insertion member 300 includes a body 310 having threads 310a, a distal portion 310b, and a proximal portion 310c. As shown in FIGS. 8, 11, and 12, the member 300 includes a triangular-shaped cannulation 310d that extends a partial length of the member 300. The threads 310a are configured for engagement with the threads 230c of the cavity 230 when the insertion member 300 is arranged within the cavity 230, as will be further explained below.

FIGS. 13-14, 14A-14B, 15, and 15A-15B show the delivery device 400 of the present disclosure for use with the anchor assembly 100 of FIG. 8. The device 400 includes a shaft 410, a handle 420 coupled to the shaft 410, and a knob 430 coupled to the handle 420. The shaft 410 includes an outer member 410a and an inner member 410b slidably disposed within and coupled to the outer member 410a. The inner member 410b includes a distal end 410b' configured for disposal within the cannulation 310d of the insertion member 300 and a proximal end 410b" coupled to the knob 430. The end 410b' is of a diameter such that it engages the wall 310d' of the cannulation 310d, thereby allowing movement of the member 30 when the knob 430 is rotated, as will be further described below. The outer member 410a includes prongs 410c located at a distal end 410a' of the outer member 410a and a proximal end 410a" coupled to the handle 420.

Prior to use, suture 440 is disposed within the through hole 250 and ends 440a,440b of the suture 440 are fixed to suture holders 450 located on handle 420. The suture 440 helps to keep anchor 200 coupled to the shaft 410. The delivery device 400 and its components, especially the knob 430, is similar to the delivery device shown and described in the '869 publication. The ends 440a,440b of the suture 440 are also housed within channels 460 that extend along the shaft 410. A suture threader 12000 is also releasably coupled to the shaft 410. Threader 12000 includes a clip 12000a and a loop of suture 12000b coupled to the clip 12000a. Suture loop 12000b is disposed within the through hole 250 and placed around the clip 12000a.

As shown in FIGS. 14A and 15A, the prongs 410c are disposed within the depressions 260. Once the anchor assembly 100 is disposed within bone, the prongs 410c help to hold the anchor 200 stationary while the insertion member 300 is moved relative to the anchor 200 via rotation of the knob 430. As will be further described below, FIG. 14A shows the location of the insertion member 300 prior to fixation of suture within the through hole 250, while FIG. 15A shows the location of the insertion member 300 after fixation of suture within the through hole 250.

Figure 14B:
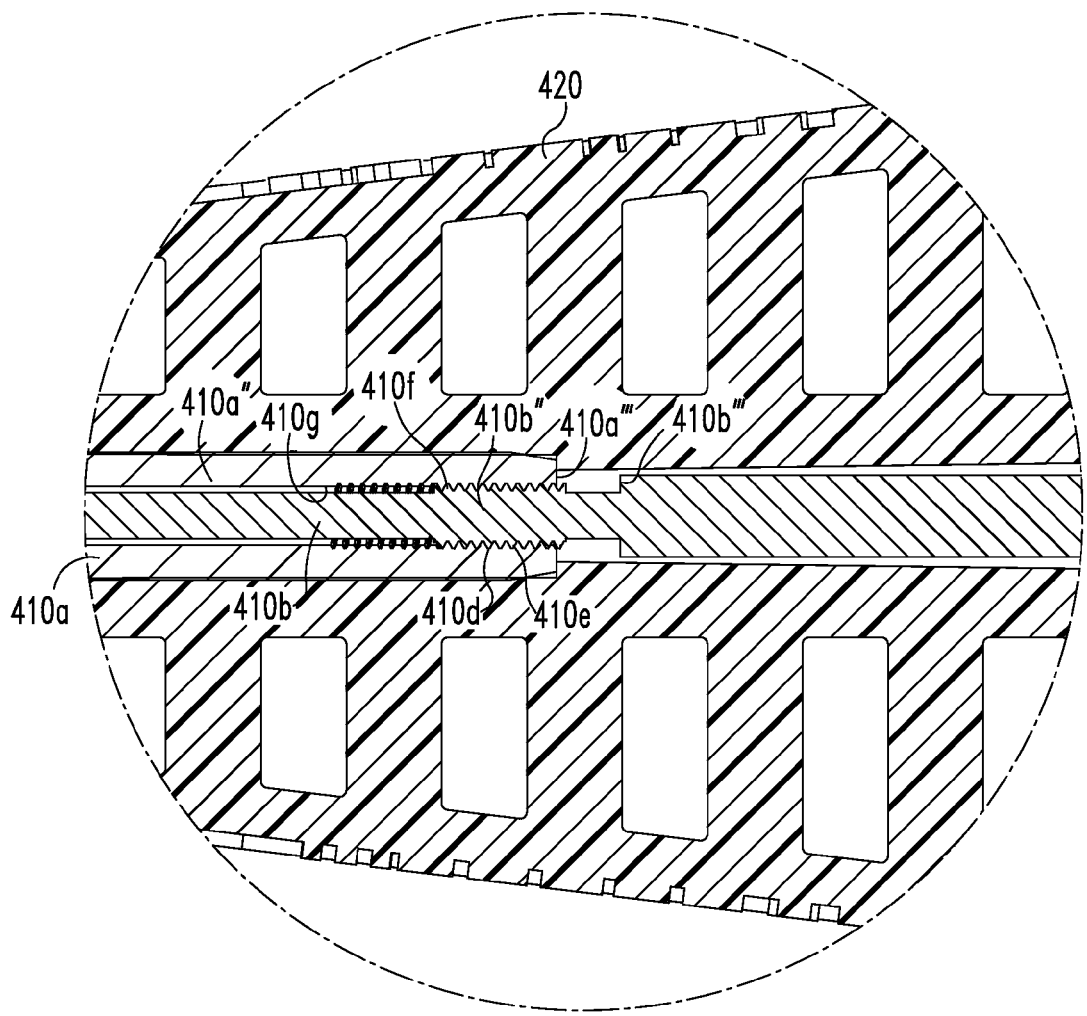
FIG. 14B shows an exploded view of the proximal ends of the outer and inner members of the delivery device of FIG. 14.
Figure 15B:
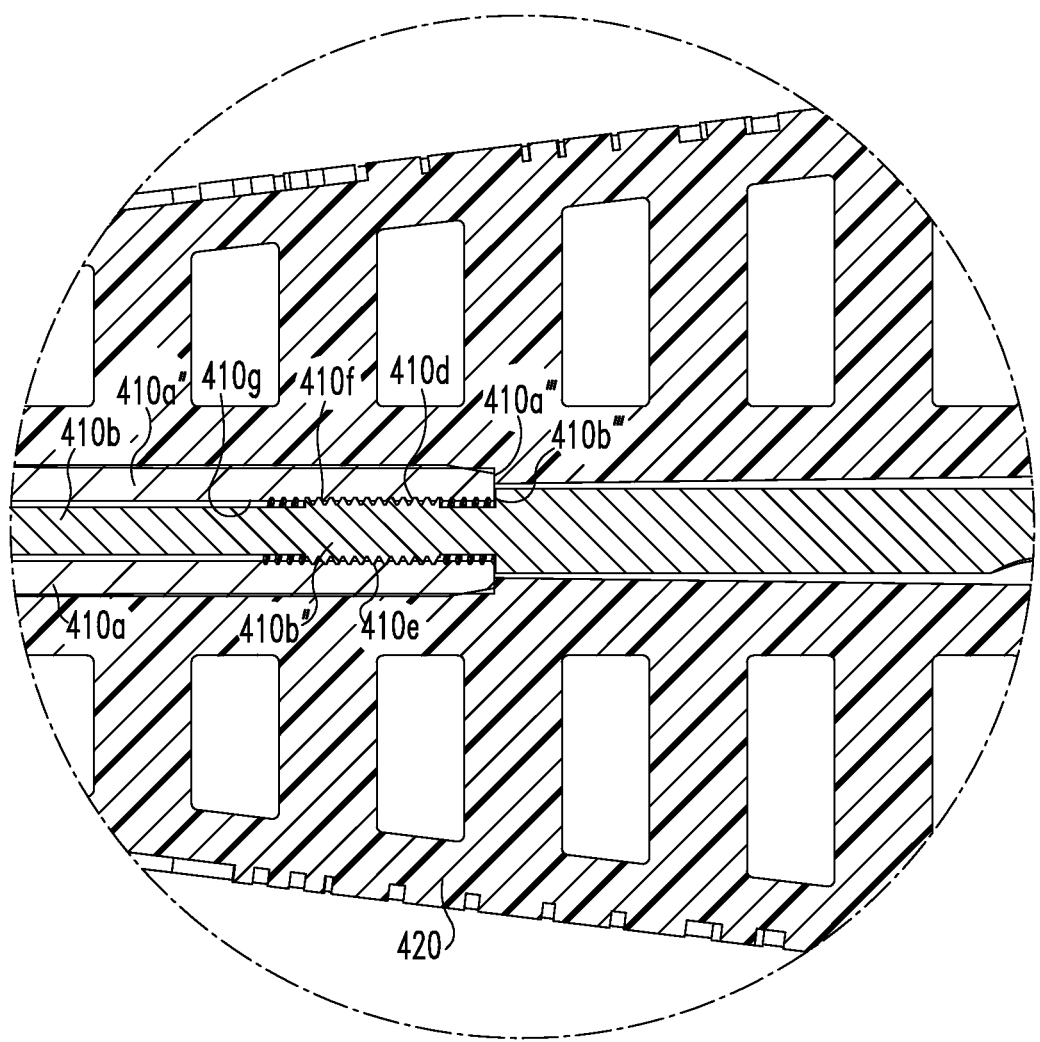
FIG. 15B shows an exploded view of the proximal ends of the outer and inner members of the delivery device of FIG. 14.

Additionally, as shown in FIGS. 14B and 15B, the proximal end 410b" of the inner member 410b includes threads 410d on an outer surface 410e of the inner member 410b and the proximal end 410a" of the outer member 410a includes threads 410f on an inner surface 410g of the outer member 410a. Threads 410f engage threads 410d to allow for coupling of the outer and inner members 410a, 410b and axial movement of the inner member 410b relative to the outer member 410a. Axial movement of the inner member 410b relative to the outer member 410a allows for axial movement of the insertion member 300 to the two locations shown in FIGS. 14A and 15A. Member 410b also includes a depth stop 410b'" that engages an end 410a'" of member 410a, as shown in FIG. 15B, once member 300 is located as shown in FIG. 15A. Interaction of the depth stop 410b'" with the end 410a'" ceases axial movement of the member 300 toward the through hole 250 and prevents the member 300 from being overly inserted into the cavity 230. The insertion member 300 is moved axially towards the through hole 250 to engage the flexible member and secure the flexible member within the cavity 230, which will be further described below.

Figure 16:
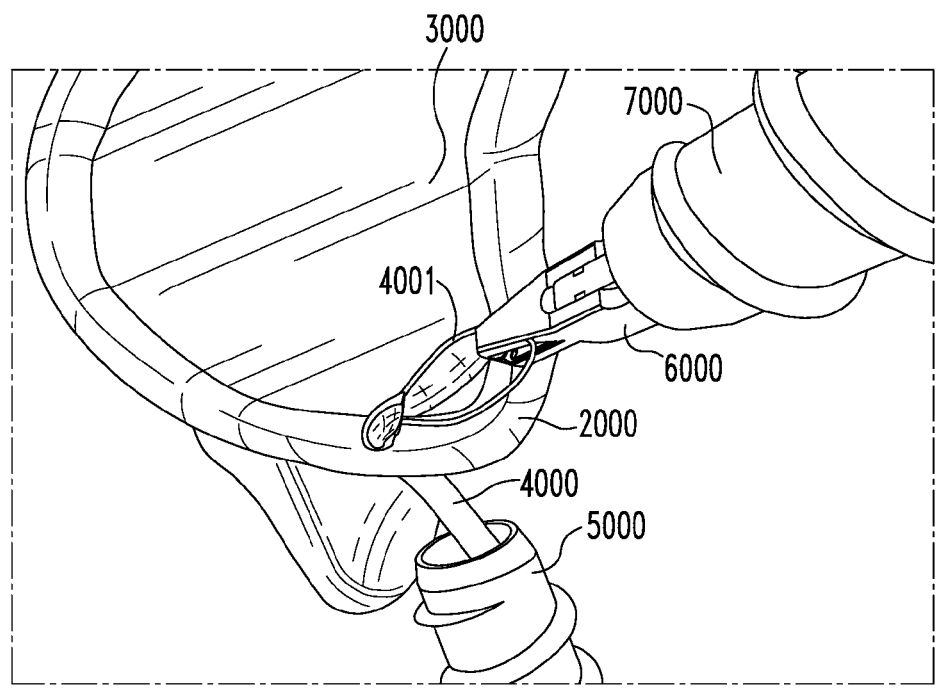
FIGS. 16-27 show a method of tissue repair via use of the delivery device and anchor assembly of FIGS. 1 and 13.
Figure 17:
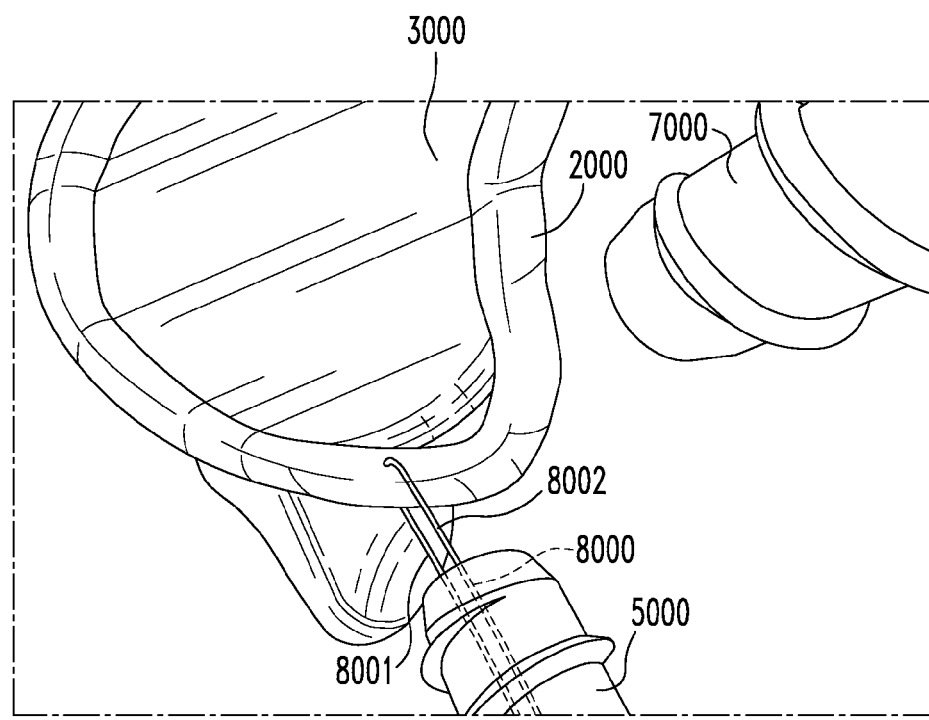

FIGS. 16-27 show the anchor assembly 10,100 of the present disclosure in use during soft tissue repair, specifically to repair labrum tears in the shoulder. As shown in FIG. 16, the labrum 2000 has been torn away from the glenoid cavity 3000 and is in need of being re-attached. FIG. 16 shows a monofilament suture loop 4001 from a suture passer 4000 being inserted through the labrum 2000 via use of a first cannula 5000. A grasper 6000 from a second cannula 7000 grabs the loop 4001 and pulls it through the second cannula 7000. Once the loop 4001 is pulled through the second cannula 7000, one end 8001 of a suture 8000 is passed through the loop 4001. The one end 8001 of the suture 8000 is pulled through the labrum 2000 and first cannula 5000 via the loop 4001, while the other end 8002 is grasped and pulled through the first cannula 5000 to have both ends 8001,8002 exiting the cannula 5000, as shown in FIG. 17.

Figure 18:
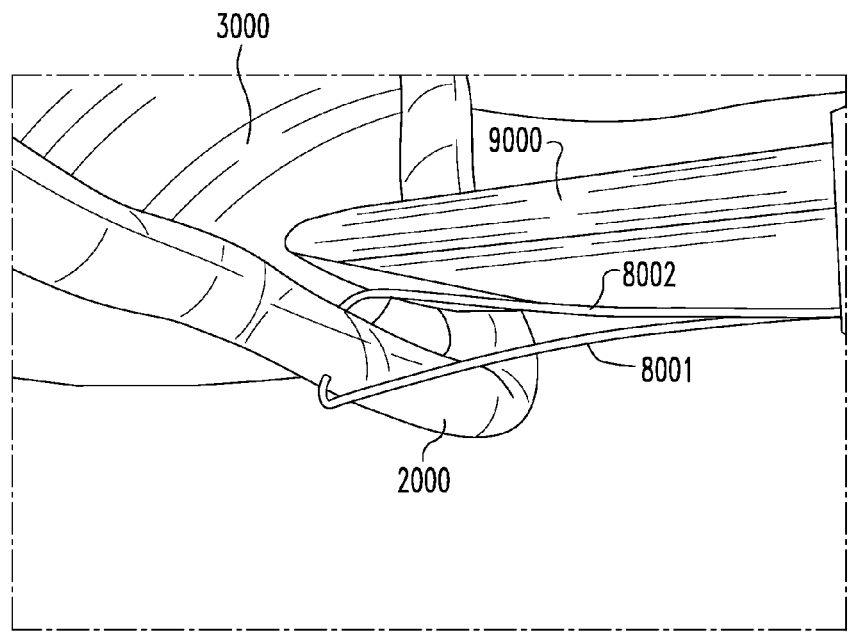
Figure 19:
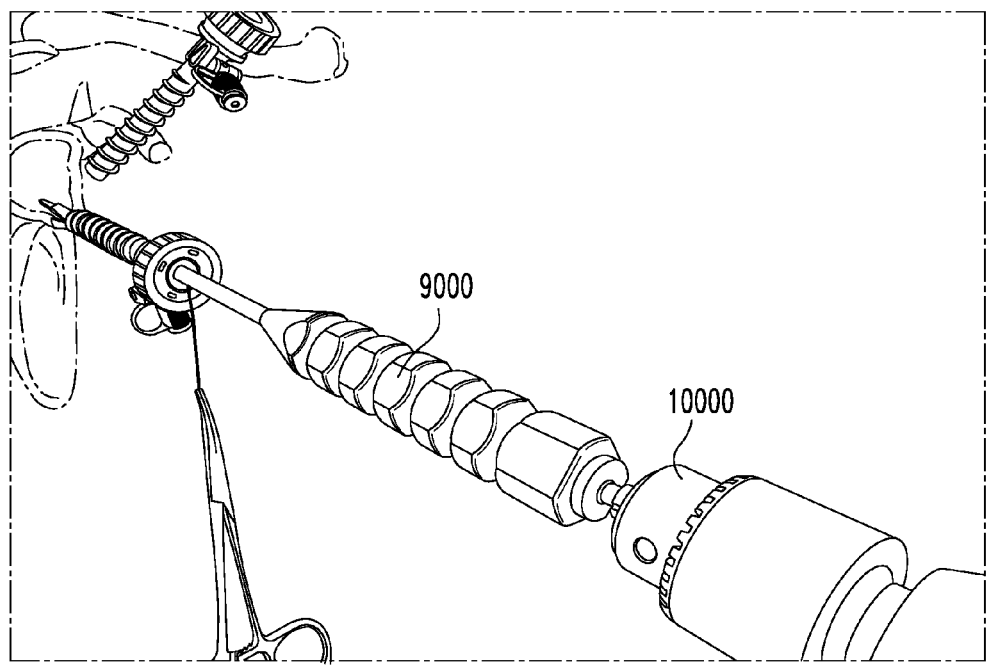
Figure 20:
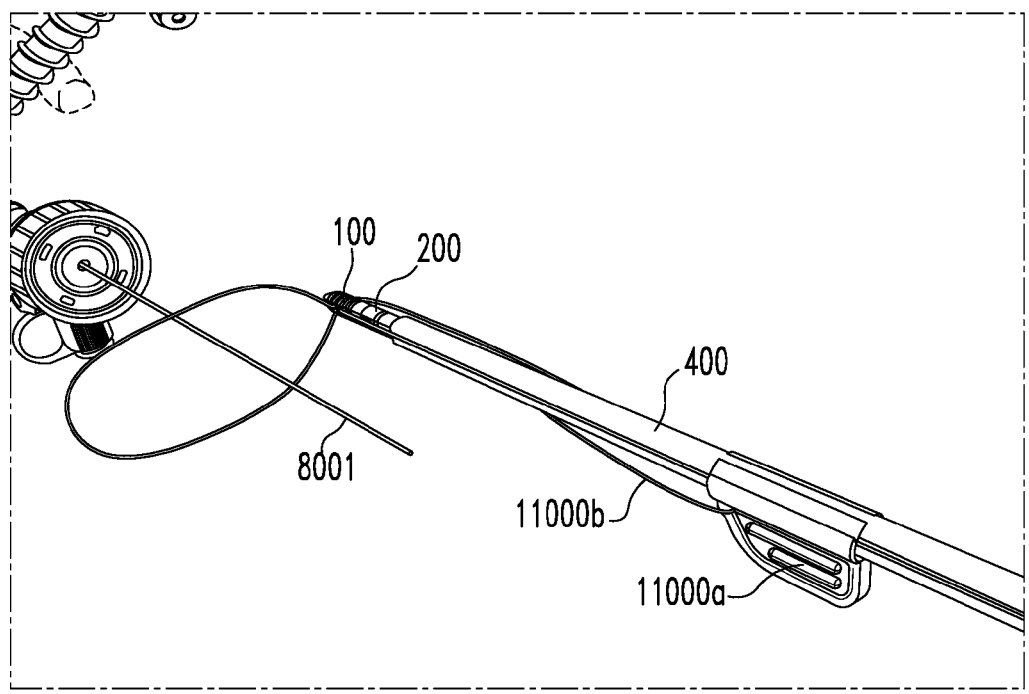
Figure 21:
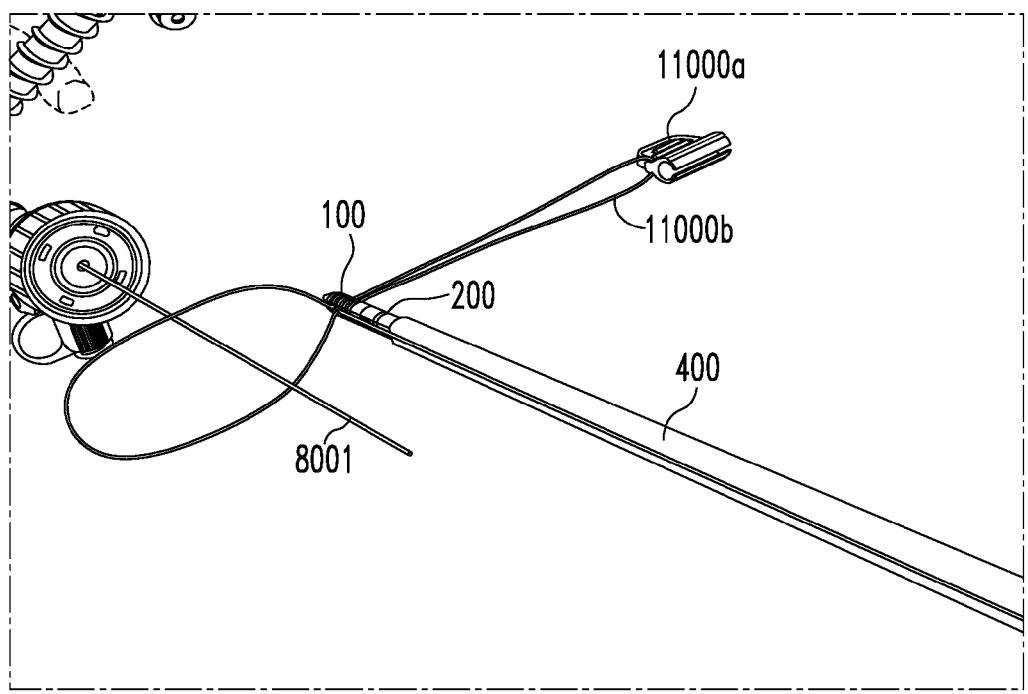
Figure 22:
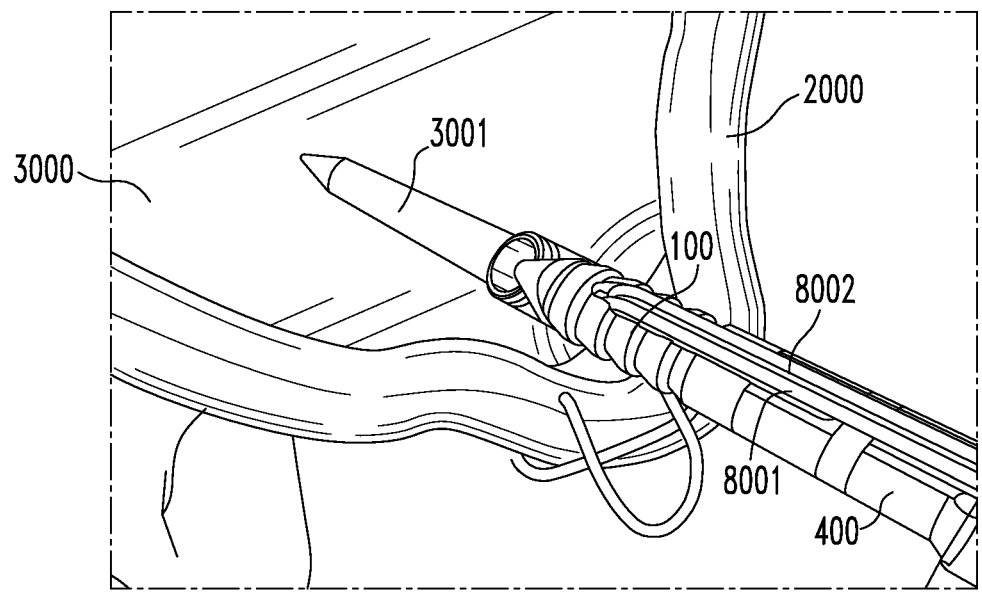
Figure 23:
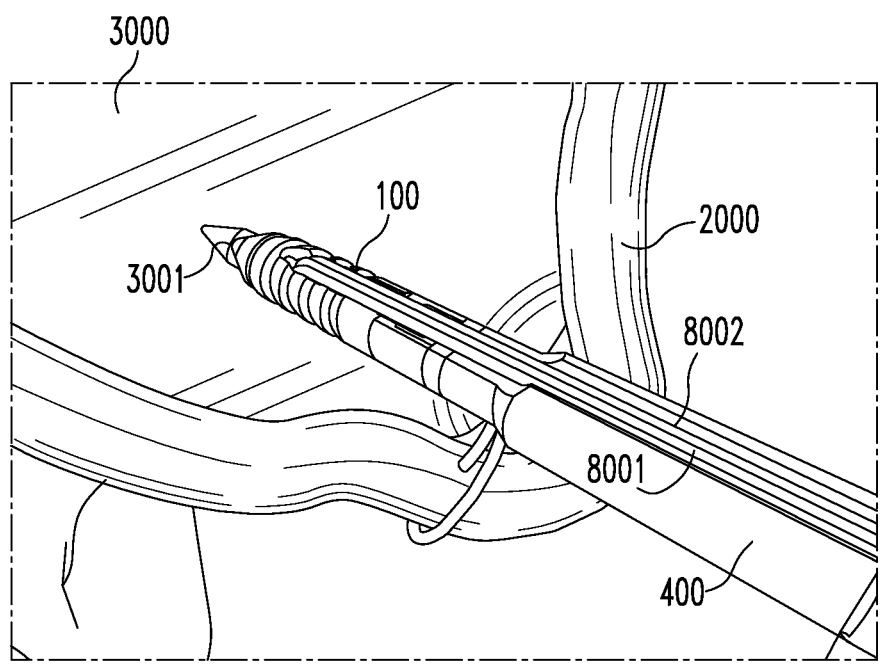
Figure 24:
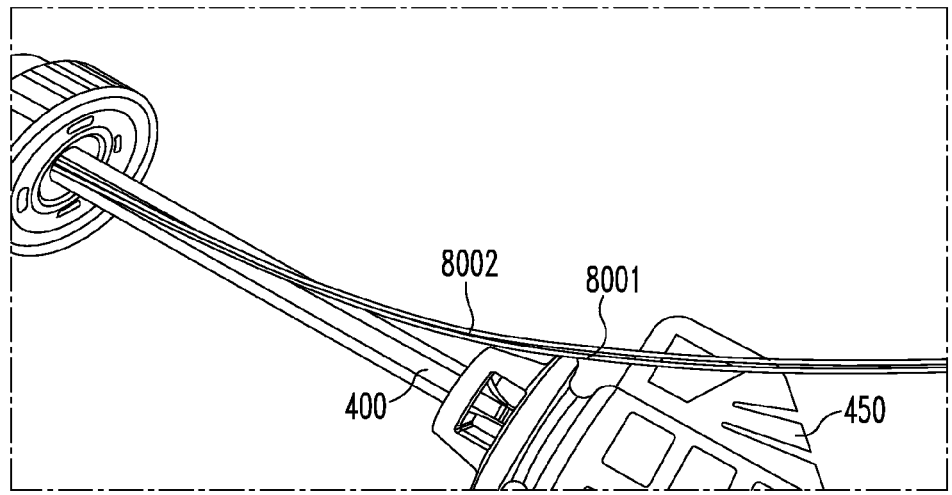
Figure 25:
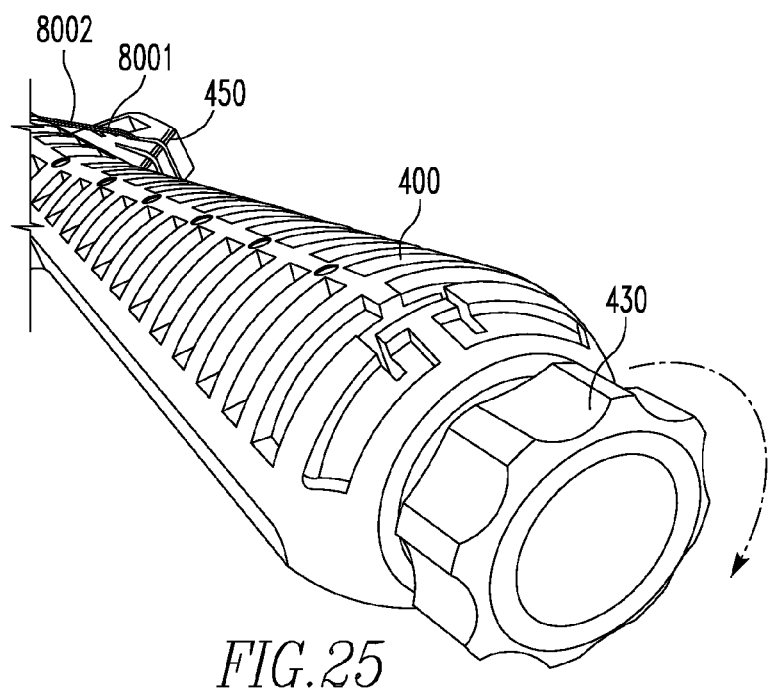

A hole 3001 is then made in the glenoid 3000 via the use of a drill guide 9000 and drill 10000, as shown in FIGS. 18 and 19. The ends 8001,8002 are placed through the suture threader loop 11000b,12000b and pulled through the through hole 25,250 of the anchor 20,200, as shown in FIGS. 20 and 21. The suture 44,440 is removed from the delivery device 40,400 prior to inserting the anchor assembly 10,100 into the hole 3001. After the anchor assembly 10,100 is inserted into the hole 3001, as shown in FIGS. 22 and 23, the suture ends 8001,8002 are tensioned and the ends 8001,8002 are locked by placing the ends 8001,8002 in the suture holder 45,450, as shown in FIG. 24, and the inner plug 30,300 is then rotated, via rotation of the knob 43,430 to fixate the suture 8000 in the cavity 23,230.

Figure 26:
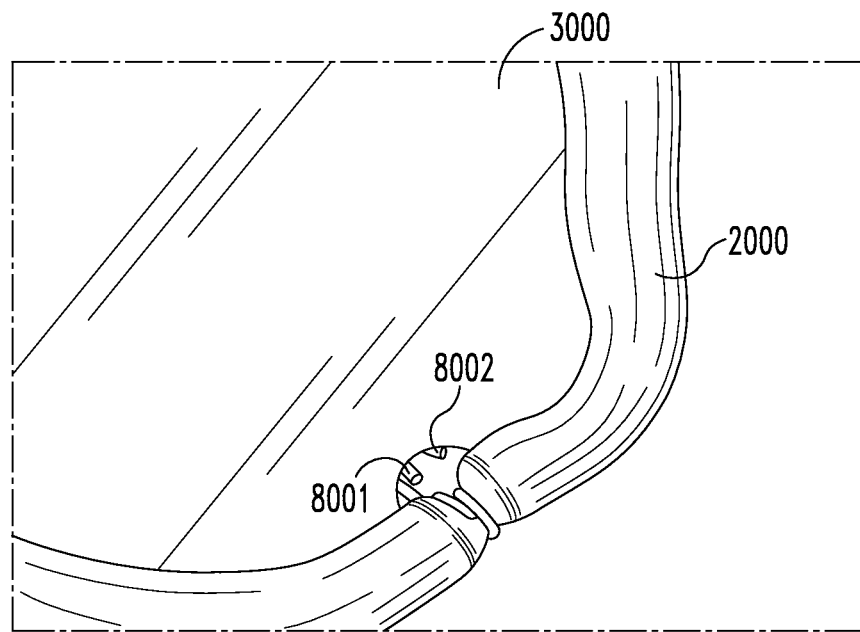
Figure 27:
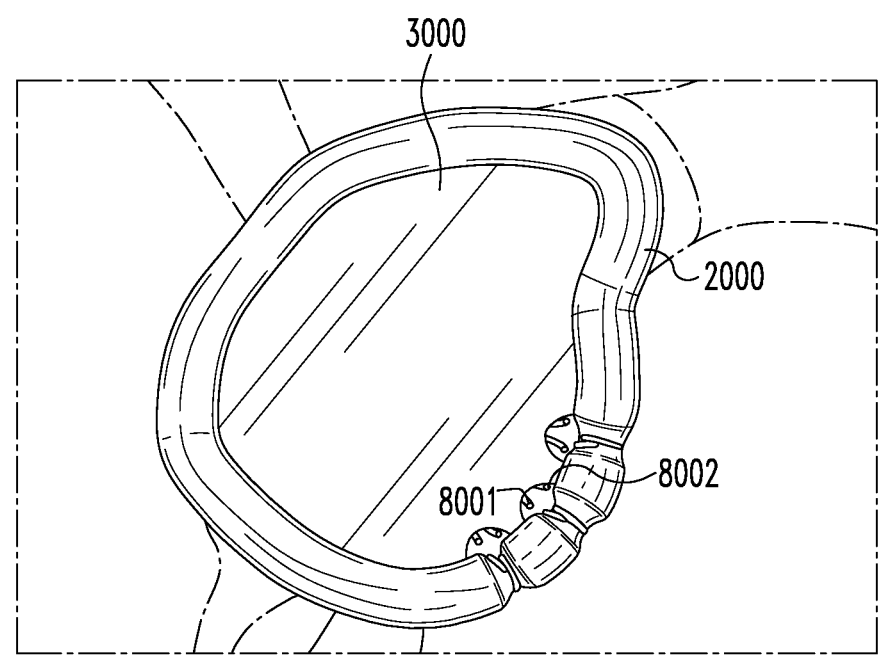

The suture ends 8001,8002 are cut, as shown in FIG. 26, and the delivery device 40,400 is removed. Additional anchor assemblies 10,100 may be inserted until the desired final repair is completed, as shown in FIG. 27. For clarity purposes, only end 8001, suture loop 12000b, and anchor assembly 100 are shown in FIGS. 20-23. However, in practice, both ends 8001,8002 are used and suture loop 11000b and anchor assembly 10 may be used rather than suture loop 12000b and anchor assembly 100.

FIGS. 28-33 show an alternative embodiment of the anchor assembly 500 of the present disclosure and its components. The assembly 500 includes the anchor 600 and the insertion member 700. The anchor 600 includes a proximal portion 610, a distal portion 620, and an inner cavity 630. The inner cavity 630 will be further described below. An opening 640 to the cavity 630 is located at the proximal portion 610 of the anchor 600. The anchor 600 also includes a transverse hole 650 extending through the anchor 600. The through hole 650 is for housing of a flexible member, such as suture. Openings 650a,b are located at each end of the through hole 650. The outer surface 670 of the proximal portion 610 also includes wings 680 for substantially reducing the possibility of removal of the anchor 600 when inserted into bone. The wings 680 are unlike barbs 28,280 in that wings 680 are longer, have more space between them, and extend further upward and outward then barbs 28,280. The outer surface 670 also includes at least two slots 690 extending from the openings 650a,b of the through hole 650. The slots 690 intersect the wings 680 and are configured for housing of the suture after positioning of the anchor 600 in bone. As shown in FIG. 10, the cavity 630 extends into and beyond the through hole 650 and includes a non-threaded proximal portion 630a and a threaded distal portion 630b. The proximal portion 630a is square-shaped to correspond with an end of the delivery device used to insert the anchor 600 into bone, as will be further described below. The proximal portion 630a also has a larger diameter and is shorter than the distal portion 630b.

The insertion member 700 includes a body 710 having a threaded proximal portion 710a and a non-threaded distal portion 710b. The proximal portion 710a has a larger diameter than the distal portion 710b. The member 700 includes a triangular-shaped cannulation 710e that extends a partial length of the member 700. The threads 710a' are configured for engagement with the threads 630c of the cavity 630 when the insertion member 700 is arranged within the cavity 630, as will be further explained below.

FIGS. 34, 34A, 35, 35, 36, 36A-36B, and 37A-37B show the delivery device 800 of the present disclosure. The device 800 includes a shaft 810, a handle 820 coupled to the shaft 810, and a knob 830 coupled to the handle 820. The shaft 810 includes an outer member 810a and an inner member 810b slidably disposed within and coupled to the outer member 810a. The inner member 810b includes a distal end 810b' configured for disposal within the cannulation 710e of the insertion member 700 and a proximal end 810b" coupled to the knob 830. The end 810b' is of a diameter such that it engages the wall 710e' of the cannulation 710e, thereby allowing movement of the member 700 when the knob 830 is rotated, as will be further described below. The outer member 810a includes a square-shaped tip 810c extending from a distal end 810a' of the outer member 810a and a proximal end 810a" coupled to the handle 820.

The handle 820 includes suture holders 850, each suture holder 850 extending from a side of the handle 820. Additionally, as shown in FIG. 34, a flexible member 900, such as a suture, is housed within the through hole 650 with each end 900a,900b of the member 900 being coupled to a holder 850. The flexible member 850 helps to hold the anchor 600 on the device 800 prior to insertion of the anchor 600 into bone. The ends 900a,900b of the suture 900 are also housed within channels 860 that extend along the shaft 810. A suture threader 13000 is also releasably coupled to the shaft 81. Threader 13000 includes a clip 13000*a* and a loop of suture 13000*b* coupled to the clip 13000*a*. Suture loop 13000*b* is disposed within the through hole 650 and placed around the clip 13000*a*. The delivery device 800 and its components, especially the knob 830, are similar to the delivery device shown and described in the '869 publication.

As shown in FIGS. 36 and 37, the tip 810*c* is disposed within the proximal portion 630*a*. Once the anchor assembly 500 is disposed within bone, the tip 810*c* helps to hold the anchor 600 stationary while the insertion member 700 is moved relative to the anchor 600. Additionally, as shown in FIG. 14A, the proximal end 810*b*" of the inner member 810*b* includes threads 810*d* on an outer surface 810*e* of the inner member 810*b* and the proximal end 810*a*" of the outer member 810*a* includes threads 810*f* on an inner surface 810*g* of the outer member 810*a*. Threads 810*f* engage threads 810*d* to allow for coupling of the outer and inner members 810*a*, 810*b* and axial movement of the inner member 810*b* relative to the outer member 810*a*.

Figure 36B:
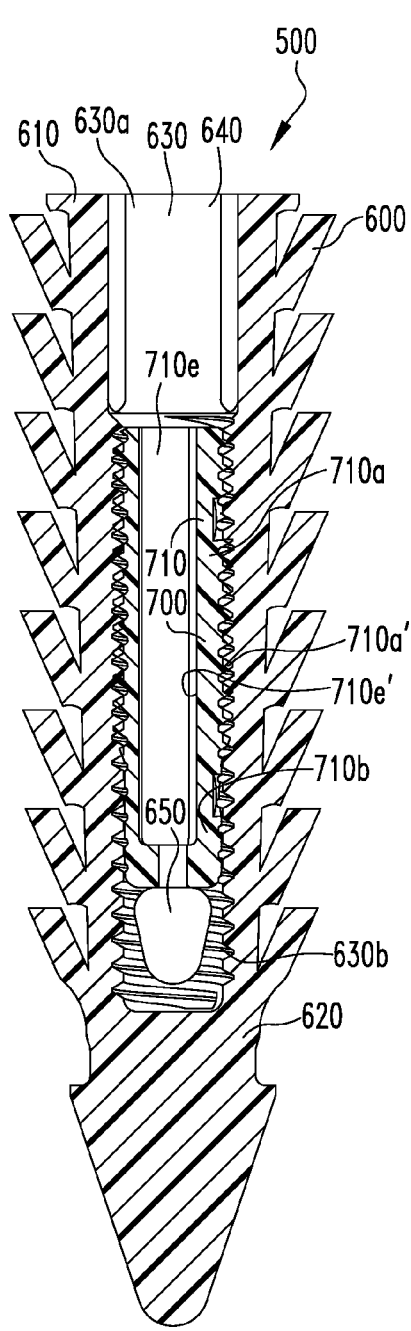
FIG. 36B shows an exploded view of the anchor assembly of FIG. 36
Figure 37B:
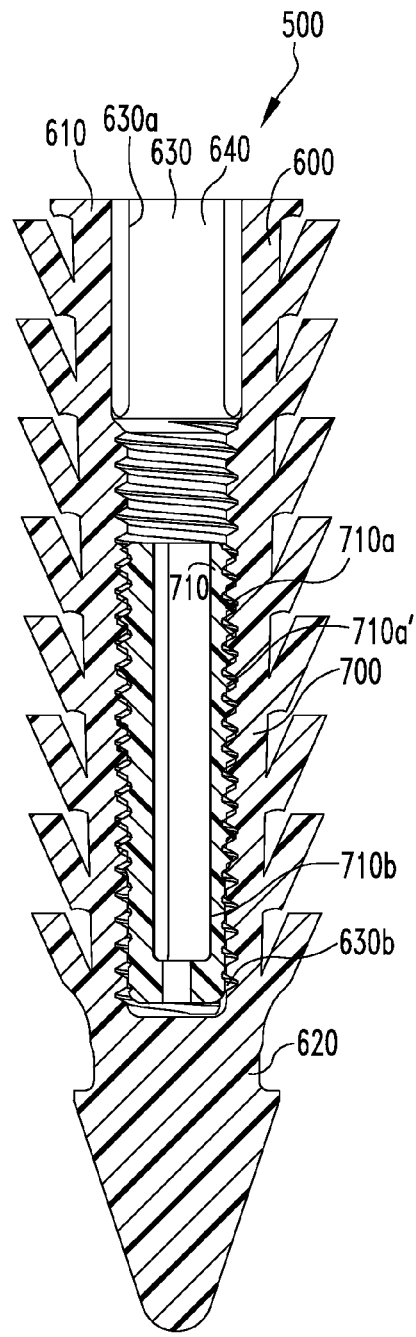
FIG. 37B shows an exploded view of the anchor assembly of FIG. 37.

Axial movement of the inner member 810*b* relative to the outer member 810*a* allows for axial movement of the insertion member 700 to the two locations shown in FIGS. 36B and 37B. Member 810*b* also includes a depth stop 810*b*''' that engages an end 810*a*''' of member 810*a*, as shown in FIG. 37A, once member 700 is located as shown in FIG. 37B. Interaction of the depth stop 810*b*''' with the end 810*a*''' ceases axial movement of the member 700 toward the through hole 650 and prevents the member 700 from being overly inserted into the cavity 630. The insertion member 700 is moved axially towards the through hole 650 to engage the flexible member and secure the flexible member within the cavity 630, which will be further described below.

During tissue repair via use of the anchor assembly 500 and the driver 800, suture from a previously placed anchor is pulled through the through hole 650. The manner in which the suture is pulled through the through hole 650 may be the same as the manner described in the '106 and '180 patent applications. The anchor assembly 500 is subsequently inserted into bone, via use of the driver 800, in the manner shown in FIG. 36B. Axial advancement of the anchor assembly 500 into the bone may occur via tapping on the handle 820. After the soft tissue is situated on the bone and the suture is located through the soft tissue, in the manner described in the '106 and '180 patent applications, the insertion member 700 is moved axially towards the distal portion 630*b*, via rotation of the knob 830 to engage the suture and secure the suture within the cavity 630, in the manner shown in FIG. 37B. For clarity purposes, only the anchor assembly 500 is shown in FIGS. 36B and 37B. However, a further description and showing of a method of tissue repair similar to the above-described method, is shown in the '106 and '180 published applications.

The components of the anchor assemblies 10,100,500 are made from a bioabsorbable polymer material via an injection molding process. However, other materials and processes may be used. In addition, the suture material is made from a bioabsorbable polymer material, but other material may be used. Furthermore, the outer surface 27, 270, 670 of the anchors 20,200,600 may include features other than barbs and wings 28,280,680 to reduce the possibility of removal of the anchor 20,200,600 and the barbs 28,280,680 may extend the entire length or a partial length of the anchor 20,200,600. Similarly, the body 31,310,710 of the insertion member 30,300,700 and the cavity 23,230,630 of the anchor 20,200,600 may include features other than threads to facilitate insertion and removal of the insertion member 30,300, 700 and the threads 31*a'*,310*a*,710*a'* may extend the entire length or a partial length of the body 31,310,710 and cavity 23,230,630. Also, for the purposes of this disclosure, the through hole 25,250,650 may be located anywhere along the length of the anchor 20,200,600. Additionally, it is within the scope of this disclosure for the anchor 20,200,600 to have more or less than two slots 29,290,690.

Additionally, for the purposes of this disclosure, the outer member 41*a*410*a* includes at least one prong 41*c*,410*c* and the anchor 20,200 includes at least one corresponding depression 26,260. Also, the cannulation 31*e*,310*e* of the insertion member 30,300 may extend an entire length of the insertion member 30,300 and may include a shape other than triangular.

The outer and inner members 41*a*,41*b*,410*a*,410*b*,810*a*, 810*b* of the delivery device 40,400,800 include a stainless steel material, but may be made from any other metal or non-metal material that is bio-compatible and strong enough to withstand the forces that are placed on the members 41*a*,41*b*,410*a*,410*b*,810*a*,810*b* during surgery. The members 41*a*,41*b*,410*a*,410*b*810*a*,810*b* may be machined, die drawn and subsequently machined, or made by any other method known to one of skill in the art. The outer and inner members 41*a*, 41*b*,410*a*,410*b*,810*a*,810*b* are coupled to the handle 42,420,820 and knob 43,430,830 respectively, via a press-fit procedure. However, other methods of coupling the handle 42,420,820 and knob 43,430,830 to the members 41*a*,41*b*,410*a*,410*b*,810*a*,810*b* are also within the scope of this disclosure. The handle 42,420,820 and knob 43,430,830 are of a non-metal material, but may be made from a metal material, and both are made via an injection molding process. However, other methods of making are also within the scope of this disclosure.

Figure 38:
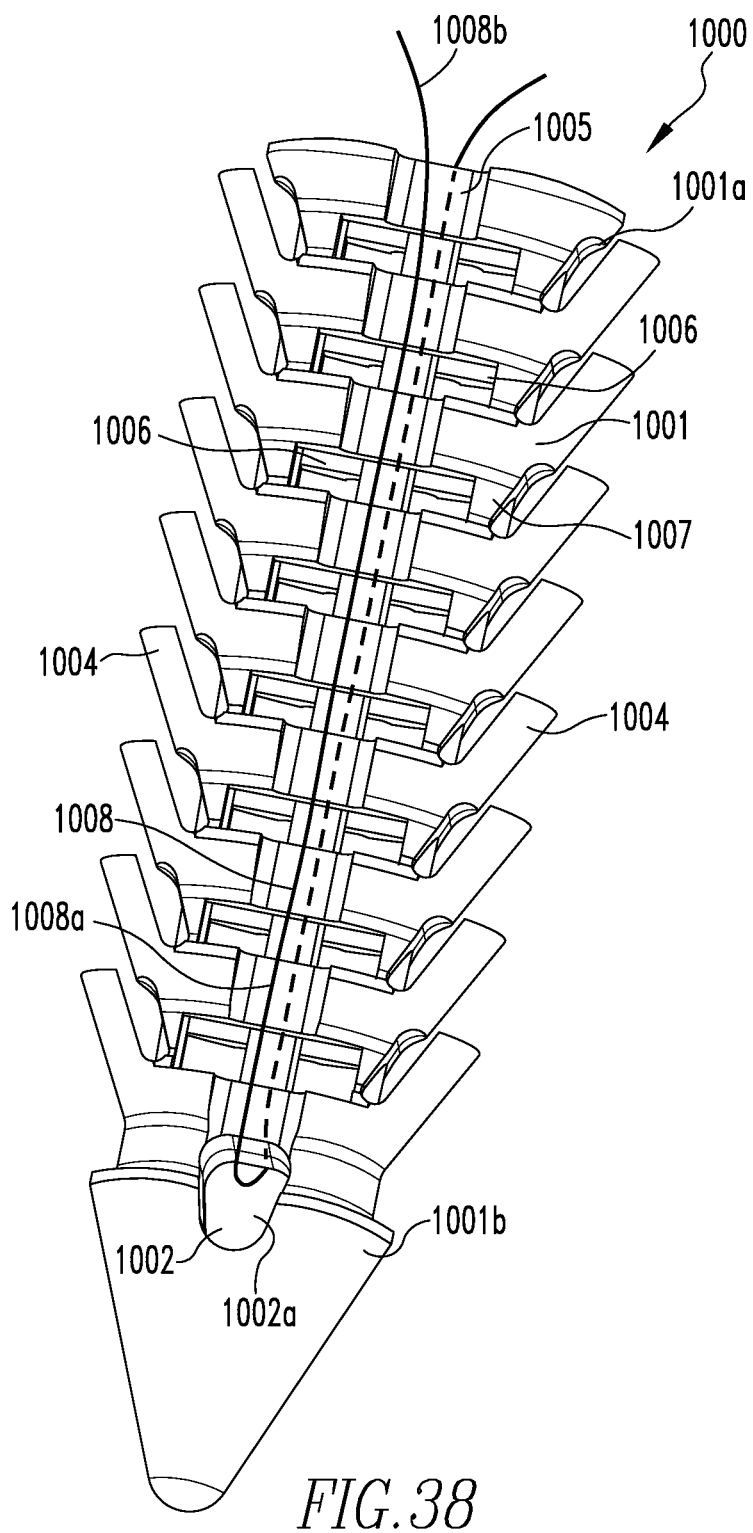
FIG. 38 shows an isometric view of a first embodiment of a fenestrated suture anchor of the present disclosure.
Figure 39:
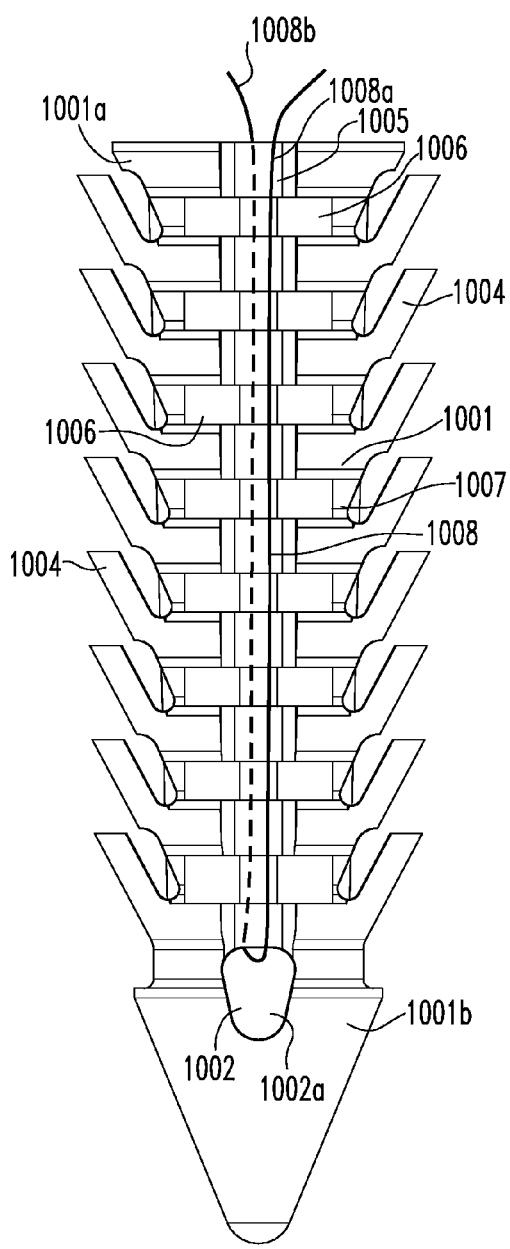
FIG. 39 shows a side view of the anchor of FIG. 38.
Figure 40:
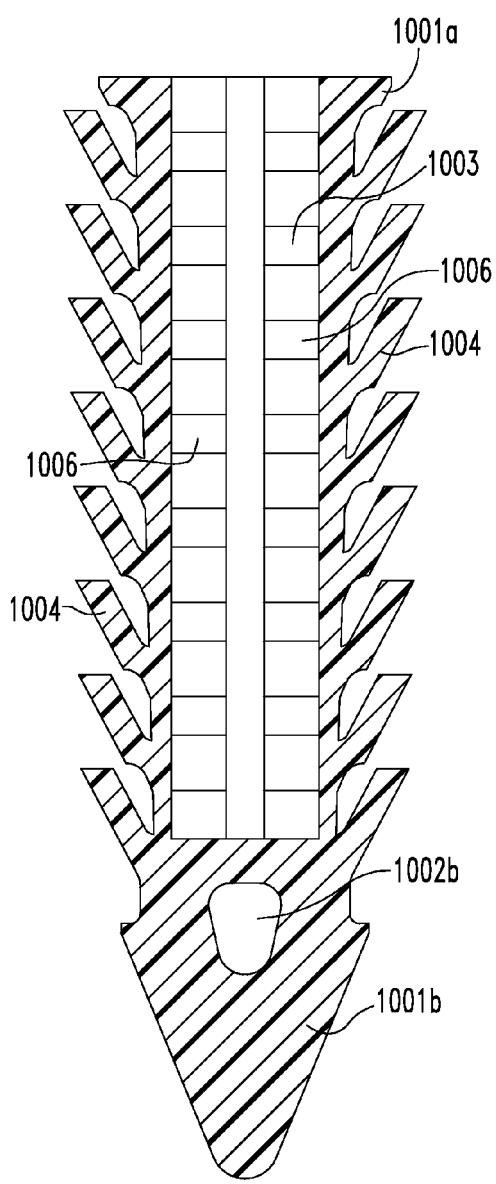
FIG. 40 shows a cross-sectional view of the anchor of FIG. 39.

FIGS. 38-40 show a first embodiment of a fenestrated suture anchor 1000 of the present disclosure. The anchor 1000 includes a body 1001 having a proximal portion 1001*a* and a distal portion 1001*b*, a transverse through hole 1002 located between the distal and proximal portions 1001*b*, 1001*a*, and a cavity 1003 extending a partial length of the body 1001. Wings 1004 exist along the body 1001 and outward from it. Similar to the wings 680, wings 1004 engage bone when the anchor 1000 is inserted into the bone, as will be further described below. The body 1001 also includes suture slots 1005 extending from openings 1002*a*, 1002*b* of the hole 1002. Additionally, there are channels 1006 extending along the body 1001 on both sides of the slots 1005. The channels 1006 extending from an outer surface 1007 of the anchor 1000 to the cavity 1003, thereby allowing the anchor 1000 to be fenestrated. The channels 1006 allow for ingrowth of tissue, such as bone, and other nutrients after insertion of the anchor 1000 into bone, as will be further described later. A suture 1008 is housed within the hole 1002 having its ends 1008*a*,1008*b* housed within the slots 1005.

Figure 41:
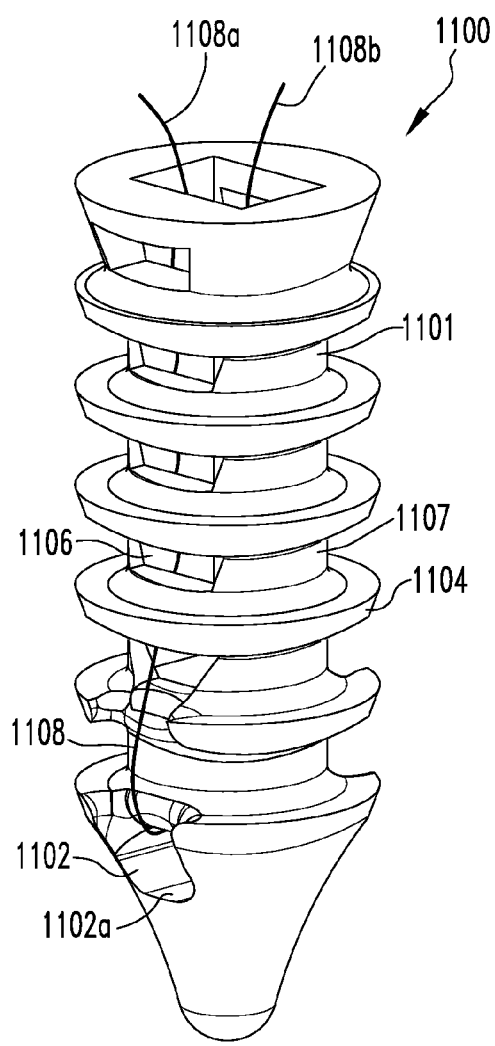
FIG. 41 shows a side elevational view of a second embodiment of a fenestrated suture anchor of the present disclosure.
Figure 42:
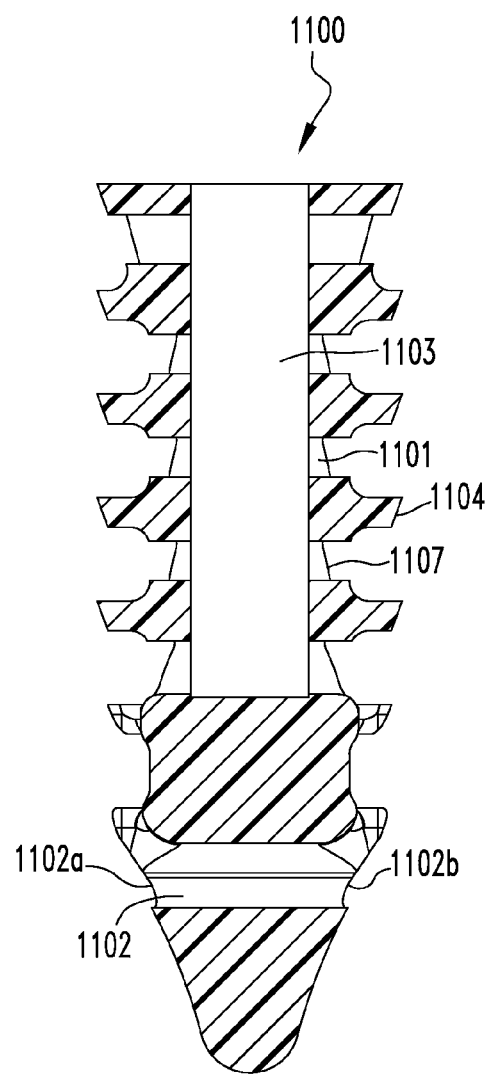
FIG. 42 shows a cross sectional view of the anchor of FIG. 41.

FIGS. 41-42 show a second embodiment of a fenestrated suture anchor 1100. The anchor 1100 includes a body 1101 having a proximal portion 1101*a* and a distal portion 1101*b*, a transverse through hole 1102 located between the distal and proximal portions 1101*b*,1101*a*, and a cavity 1103 extending a partial length of the body 1101. Barbs 1104 exist along the body 1101 and extend outward from it. Similar to the barbs 28,280, barbs 1104 engage bone when the anchor 1100 is inserted into the bone, as will be further described below. The body 1101 also includes channels 1106 extending along the body 1101. The channels 1106 extending from an outer surface 1107 of the anchor 1100 to the cavity 1103, thereby allowing the anchor 1100 to be fenestrated. The channels 1106 allow for ingrowth of tissue, such as bone, and other nutrients after insertion of the anchor 1100 into bone, as will be further described later. A suture 1108 is housed within the hole 1102 having its ends 1108a,1108b extend through openings 1102a,1102b and then back through the cavity 1103, as shown in FIG. 41.

Figure 43:
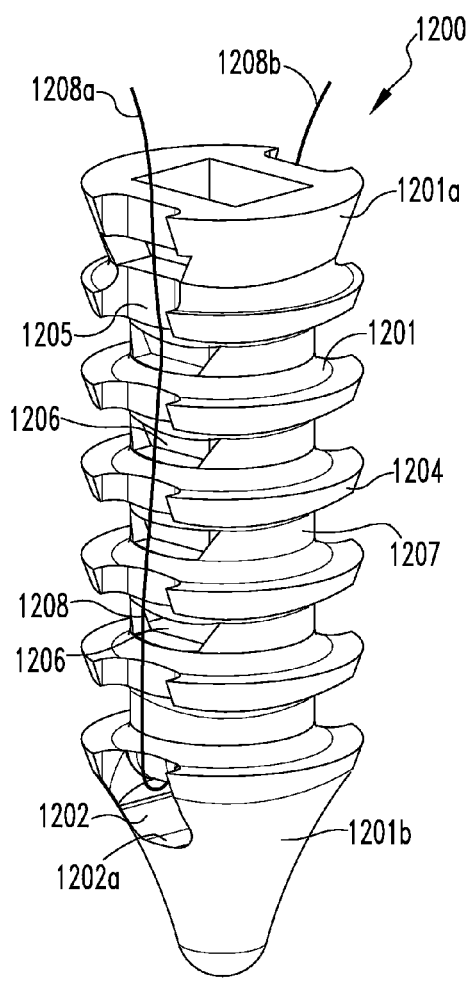
FIG. 43 shows a side elevational view of a third embodiment of a fenestrated suture anchor of the present disclosure.
Figure 44:
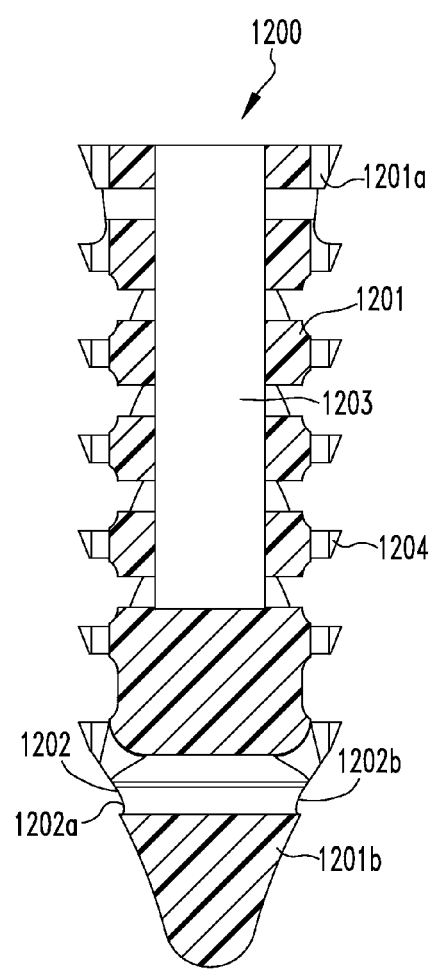
FIG. 44 shows a cross-sectional view of the anchor of FIG. 43.

FIGS. 43-44 show a first embodiment of a fenestrated suture anchor 1200 of the present disclosure. The anchor 1200 includes a body 1201 having a proximal portion 1201a and a distal portion 1201b, a transverse through hole 1202 located between the distal and proximal portions 1201b, 1201a, and a cavity 1203 extending a partial length of the body 1201. Barbs 1204 exist along the body 1201 and extend outward from it. Similar to the barbs 28,280, barbs 1204 engage bone when the anchor 1200 is inserted into the bone, as will be further described below. The body 1201 also includes suture slots 1205 extending from openings 1202a, 1202b of the hole 1202. Additionally, there are channels 1206 extending along the body 1201 interspaced with the slots 1205. The channels 1206 extend from an outer surface 1207 of the anchor 1200 to the cavity 1203, thereby allowing the anchor 1200 to be fenestrated. The channels 1206 allow for ingrowth of tissue, such as bone, and other nutrients after insertion of the anchor 1200 into bone, as will be further described later. A suture 1208 is housed within the hole 1202 having its ends 1208a,1208b housed within the slots 1205.

During repair of tissue via use of the suture anchors 1000,1100,1200, a delivery device having a handle and a shaft may be used to deliver the anchors into bone. An end of the shaft may be inserted into the cavity of the anchors and may have the same shape as cavity. The anchors 1000,1100,1200 are designed to be inserted into bone via axial motion. The torn tissue may then be placed on the bone, adjacent the anchors 1000,1100,1200. Subsequently, the suture may then be pulled through the tissue and tied to attach the tissue to the bone. A hole may be drilled in the bone prior to inserting the anchors 1000,1100,1200 into the bone.

Figure 28:
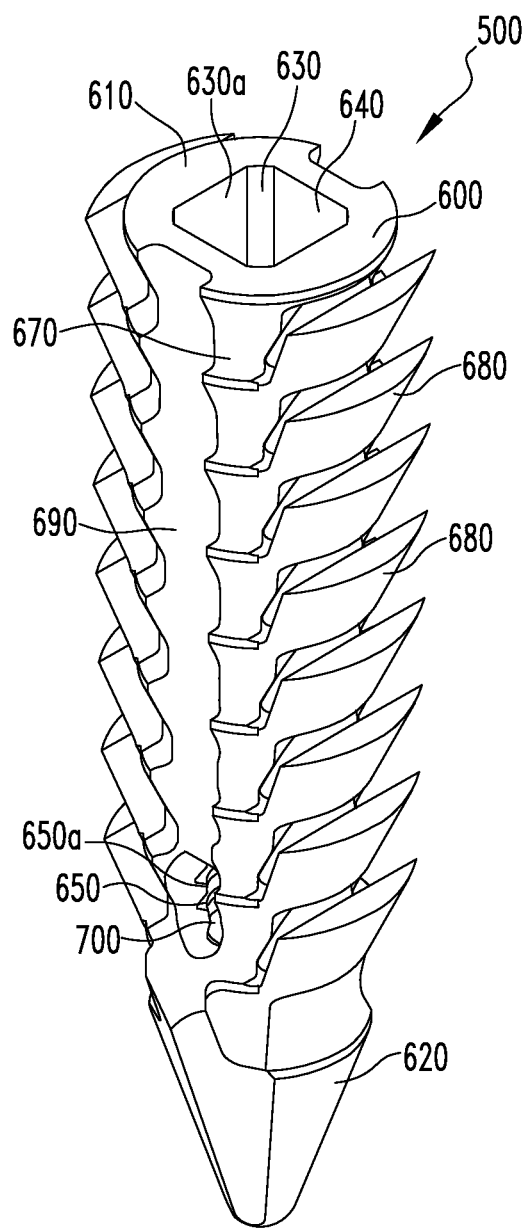
FIG. 28 shows a side elevational view of a third embodiment of the anchor assembly of the present disclosure.
Figure 29:
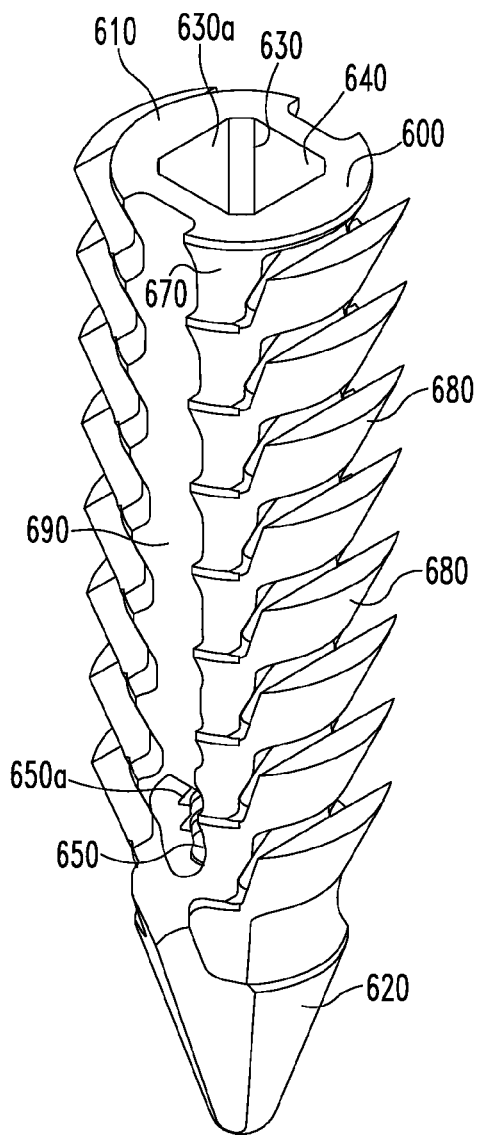
FIG. 29 shows a side elevational view of the anchor of the anchor assembly of FIG. 28.
Figure 30:
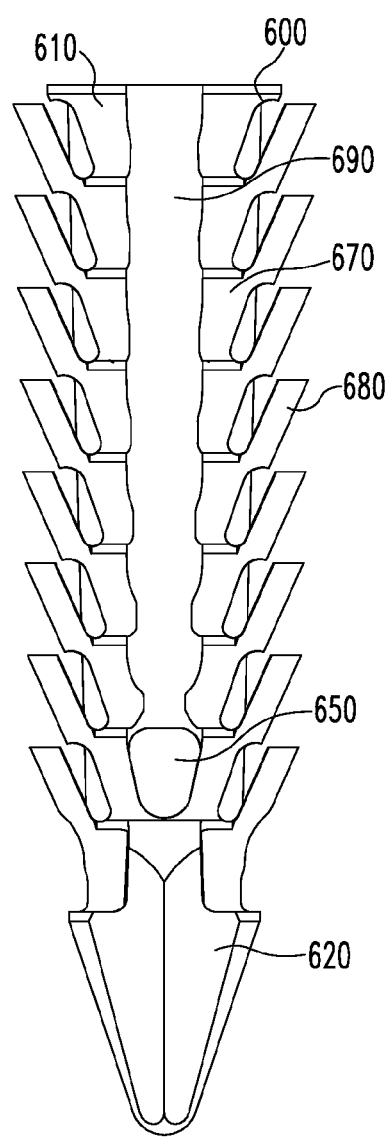
FIG. 30 shows a side view of the anchor of FIG. 29.
Figure 31:
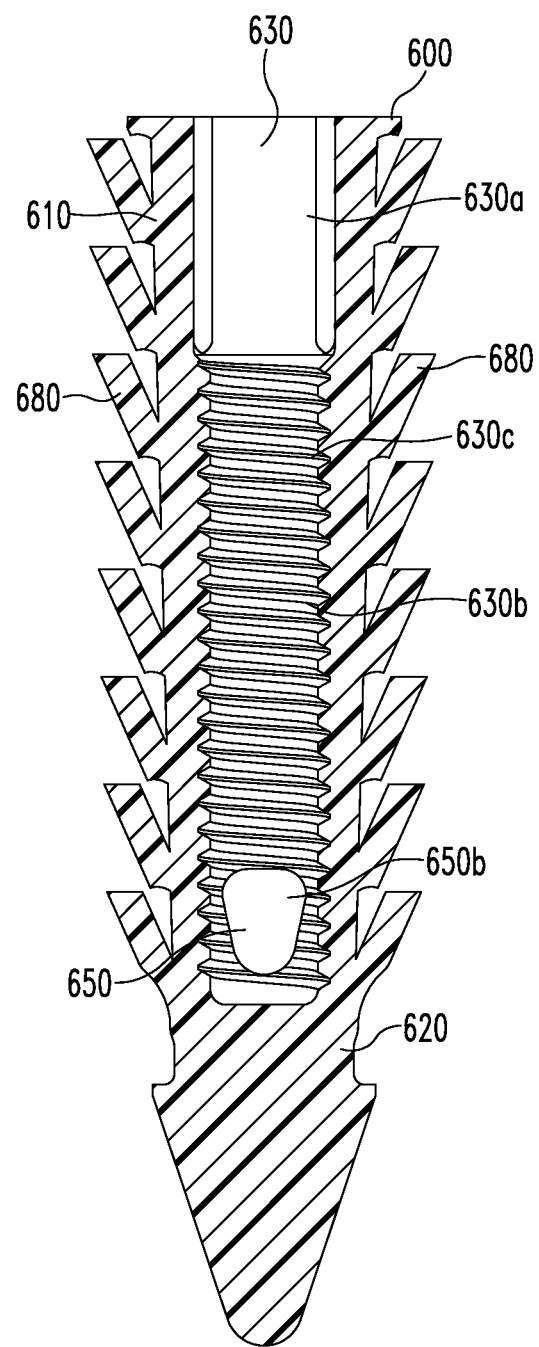
FIG. 31 shows a cross-sectional view of the anchor of FIG. 29.
Figure 32:
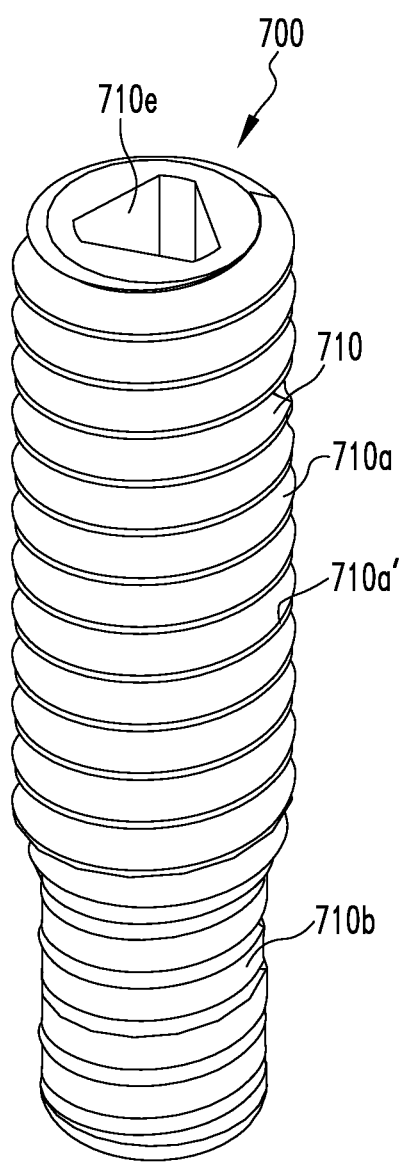
FIG. 32 shows a side elevational view of the insertion member of the anchor assembly of FIG. 28.
Figure 33:
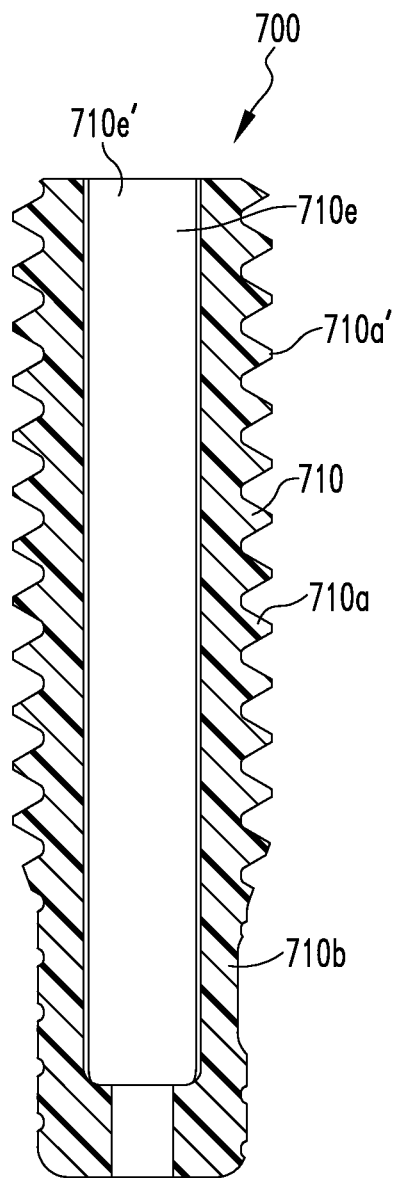
FIG. 33 shows a cross-sectional view of the insertion member of FIG. 32.
Figure 34A:
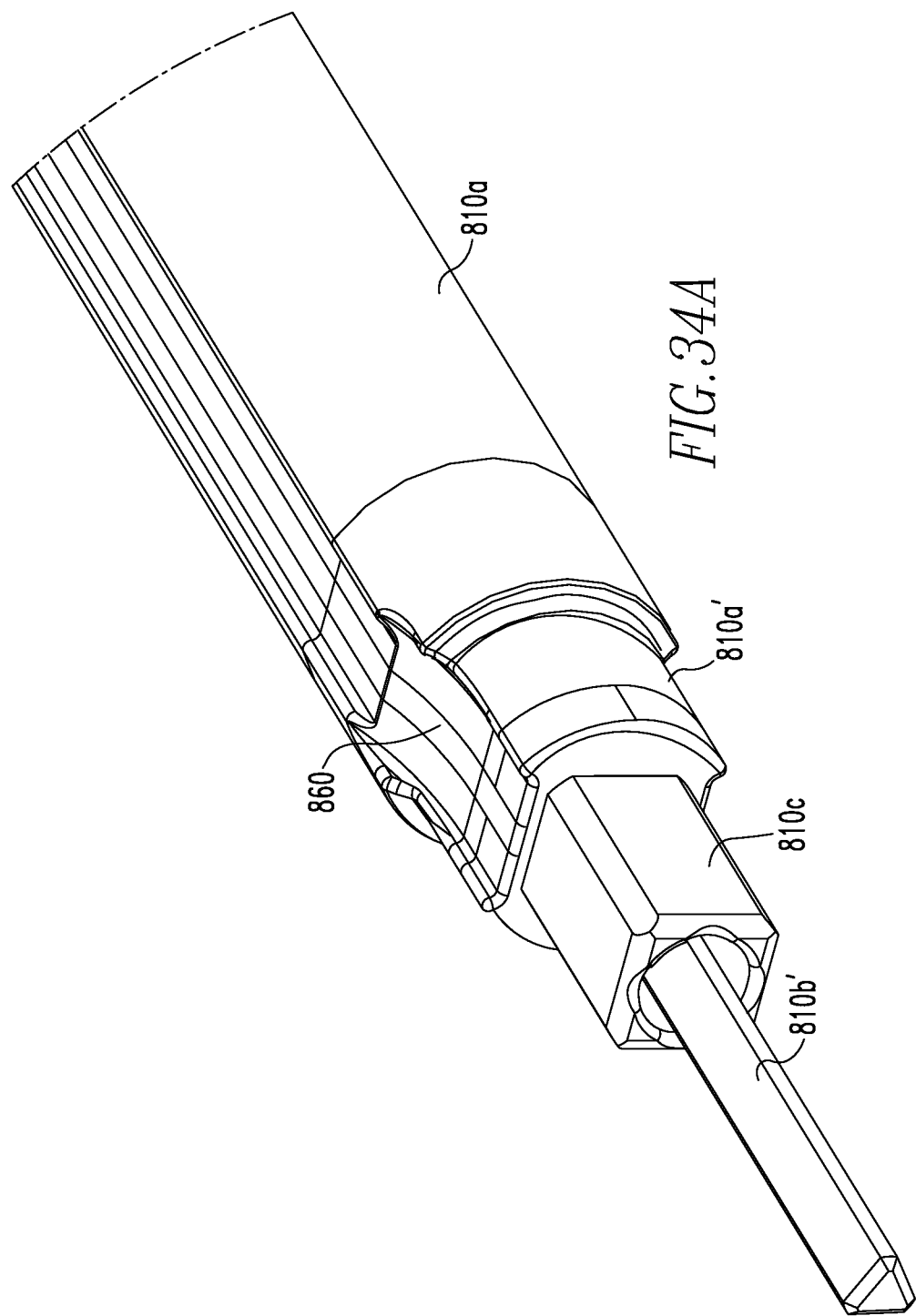
FIG. 34A shows an exploded view of the distal end of the delivery device of FIG. 34.
Figure 35:
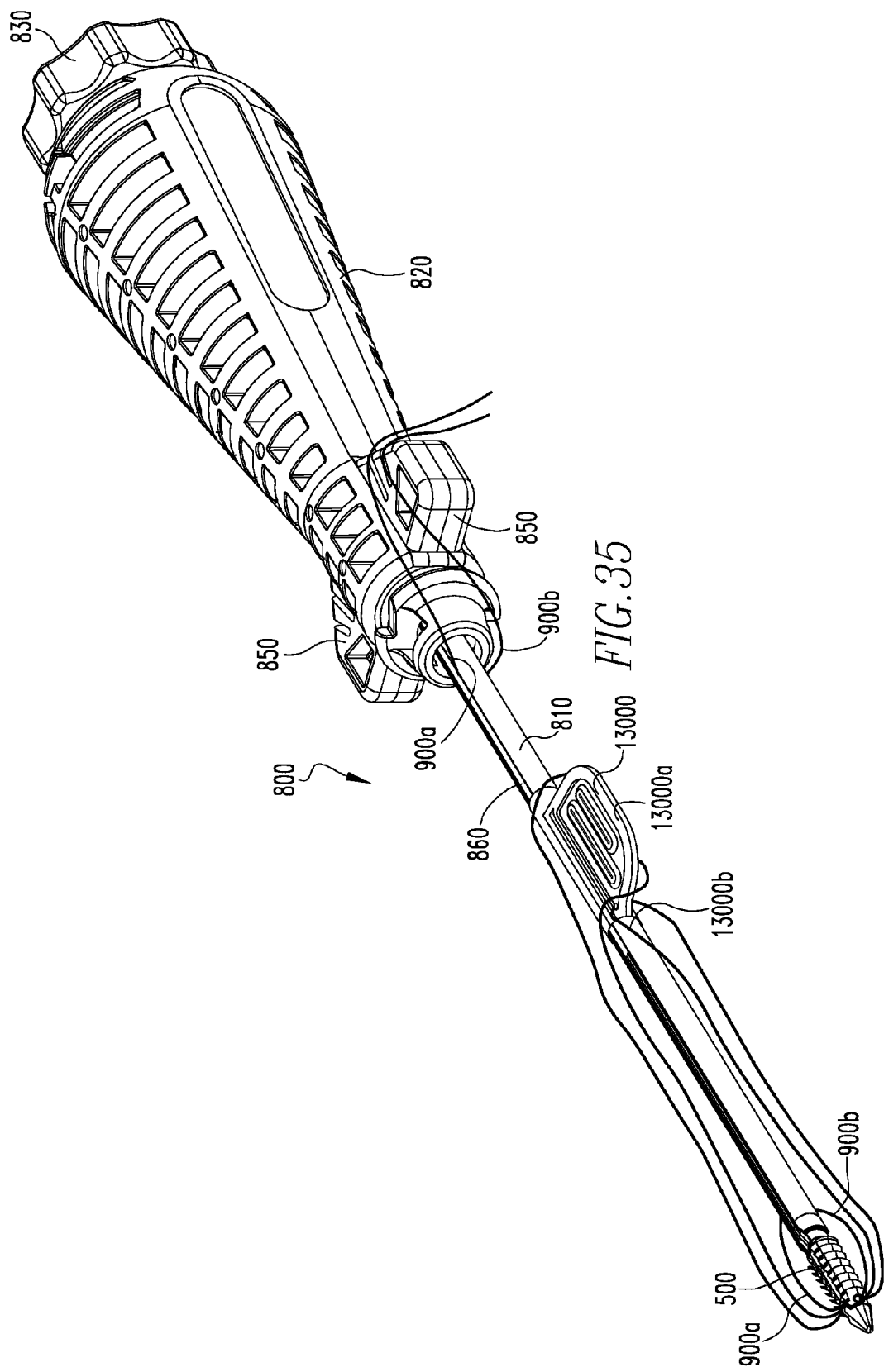
FIG. 35 shows an isometric view of the delivery device and anchor assembly of FIGS. 28 and 34.

FIGS. 45-50 show anchor assemblies 1300,1400,1500 similar to the anchor assemblies 10 of FIGS. 1, 8, and 28. The anchor assemblies 1300,1400,1500 are similar to the anchor assemblies 10,100,500 of FIGS. 1, 8, and 28 and the anchor assemblies shown and described in US Patent Application Publication No. 20090112270, the disclosure of which is incorporated herein by reference in its entirety, and the '869 publication mentioned above. FIGS. 45-50 only show the anchors 1310,1410,1510 of the assemblies 1300, 1400,1500. Although for the purposes of this disclosure, an insertion member, similar to the insertion members shown in the above mentioned figures and publications, would also be used with the anchors 1310,1410,1510. However, it is possible that the anchors 1310,1410,1510 could be used without insertion members, thereby being used in a similar manner to anchors 1000,1100,1200 during surgery.

Figure 45:
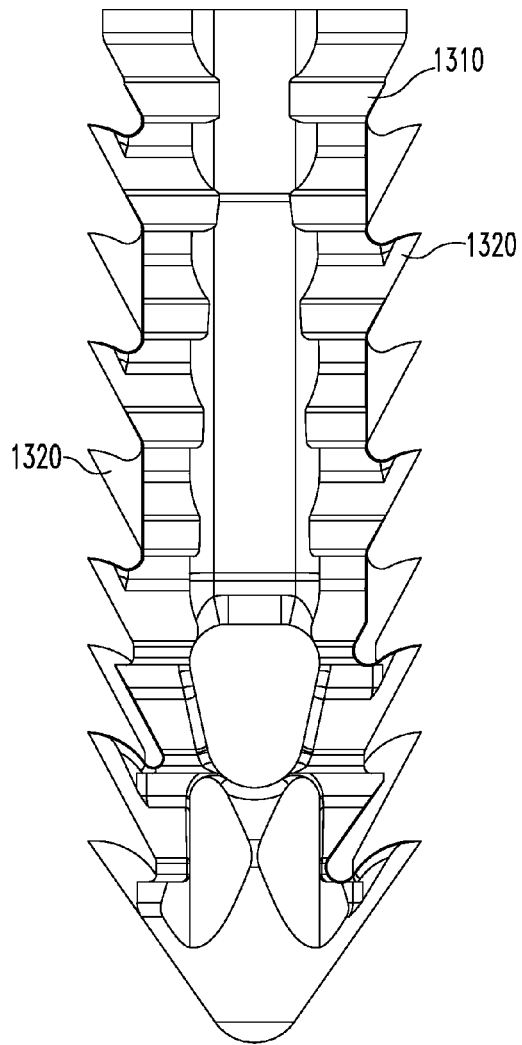
FIG. 45 shows a side view of a fourth embodiment of the anchor assembly of the present disclosure.
Figure 46:
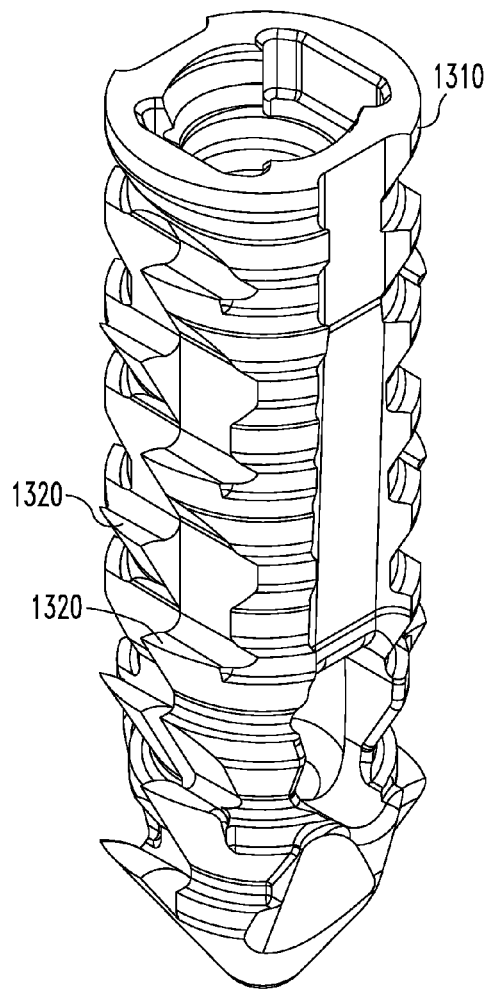
FIG. 46 shows a side elevational view of the anchor assembly of FIG. 45.
Figure 47:
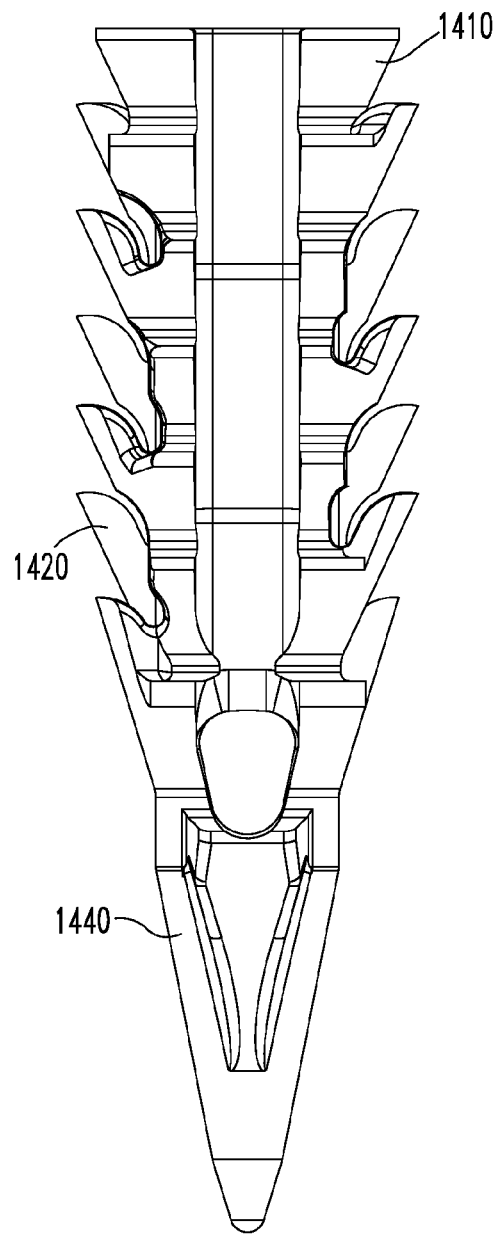
FIG. 47 shows a side view of a fifth embodiment of the anchor assembly of the present disclosure.
Figure 48:
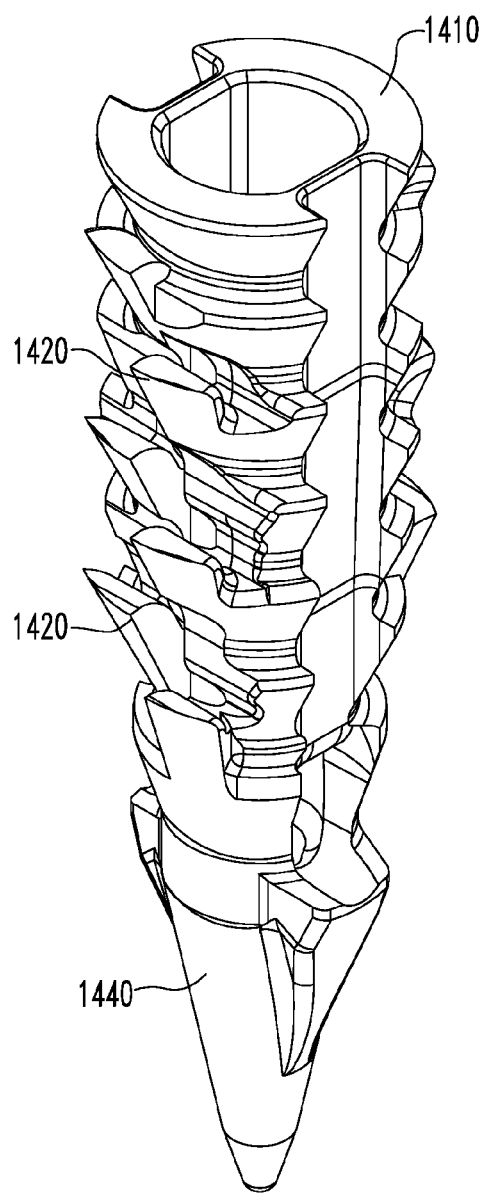
FIG. 48 shows a side elevational view of the anchor assembly of FIG. 47.

FIGS. 45-46 show an anchor 1310 having barbs 1320 that extend outward from the body 1330 of the anchor 1310 and along its entire length on both sides. The barbs 1320 alternate in direction along the length of the anchor 1310. Similar to wings 680, extending the barbs 1320 outward from the body 1330 increases the overall surface area of the barbs 1320 and allows flexibility, which improves resistance to anchor pull-out, thereby reducing the possibility of removal of the anchor 1300 when inserted into bone. FIGS. 47-50 show anchors 1410,1510, which include barbs 1420, 1520, similar in design and orientation, to barbs 1320 of anchor 1310. Unlike anchor 1310, the barbs 1420,1520 do not extend along the entire length of the anchor 1410,1510 and the distal end 1440,1540 of the anchor 1410,1510 is pointed thereby making it possible to insert the anchor 1410,1510 into bone without first creating a hole in the bone.

Figure 51:
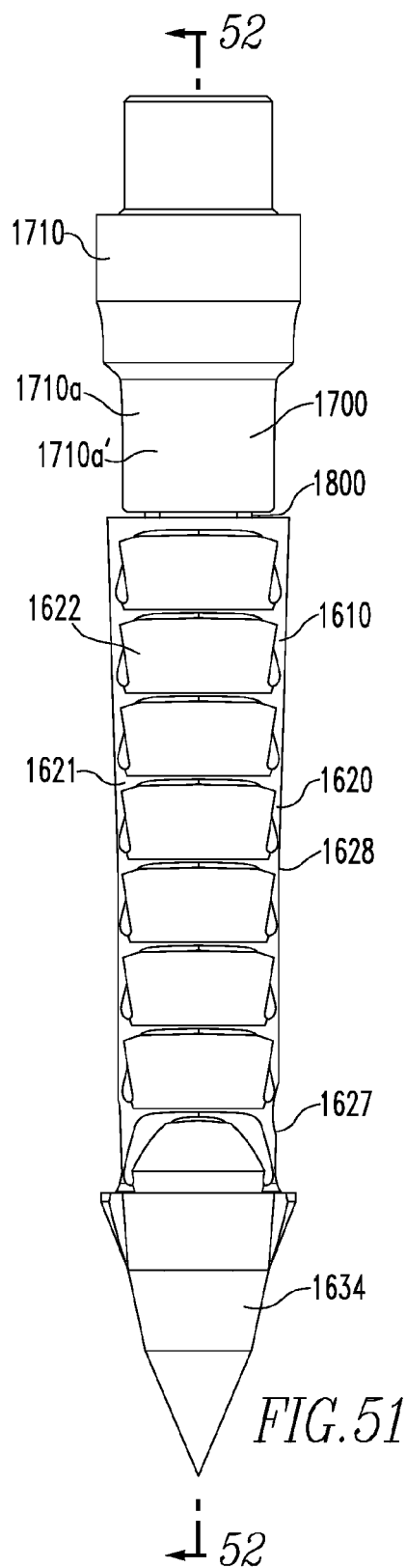
FIG. 51 shows a side view of a seventh embodiment of the anchor assembly of the present disclosure.
Figure 52:
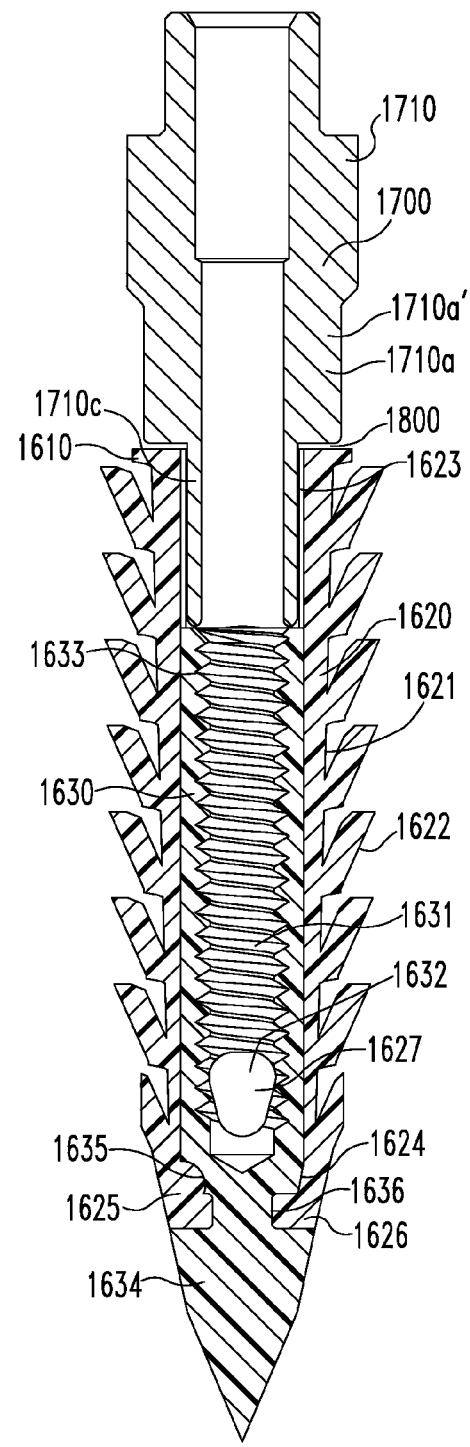
FIG. 52 shows a cross-sectional view of the anchor assembly of FIG. 51.

FIGS. 51 and 52 show an anchor 1610 that includes an outer body 1620 and an inner body 1630 disposed within the outer body 1620. The outer body 1620 includes an outer surface 1621 having wings 1622, similar to wings 680, and an inner cavity 1623. The distal end 1624 of the inner cavity 1623 includes a first feature 1625 and a second feature 1626, which will be more fully explained below in relation to the inner body 1630. Similar to the anchors described above, the outer body 1620 also includes a transverse hole 1627 and slots 1628. Similar to the anchors described above, the inner body 1630 includes a threaded inner cavity 1631, a through hole 1632, a proximal portion 1633, and a distal portion 1634. The inner body 1630 includes a first feature 1635 and a second feature 1636, both of which are located between the proximal and distal portions 1633,1634 and which will be more fully explained below in relation to the outer body 1620. The inner body 1630 is disposed within the outer body 1620 such that the outer body first feature 1625 is located within the inner body first feature 1635 and the outer body second feature 1626 is located within the inner body second feature 1636. The first features 1625,1635 are shaped so as to substantially reduce the possibility of the inner body 1630 rotating in relation to the outer body 1620 during repair, as will be more fully described below. The second features 1626,1636 are shaped so as to substantially reduce the possibility of the inner body 1630 from moving axially in relation to the outer body 1620 during insertion of the anchor 1610 into bone, as will be more fully described below. Additionally, the through holes 1627,1632 are aligned.

Similar to anchors 1310,1410,1510, anchor 1610 is part of an anchor assembly. However, for clarity purposes, the anchor 1610 is shown without an inner member. The distal portion 1634 of the inner body 1630 is pointed and the proximal portion 1633 does not extend the entire length of the inner cavity 1623, the purposes of which will be described later.

During insertion of the anchor 1610 into bone, a delivery device 1700, similar to delivery device 800, is used. For clarity purposes, only the outer member 1710a of the shaft 1710 is shown in FIGS. 51 and 52. The outer member 1710a is inserted into the anchor 1610 such that the square-shaped tip 1710c is inserted into the inner cavity 1623. The tip 1710c engages the inner body 1630 such that there is a clearance 1800 between the distal end 1710a' of the shaft 1710 and the anchor 1610. During insertion of the anchor 1610 into bone, the outer member 1710a only engages the inner body 1630, thereby asserting all of the axial force of the outer member 1710a on the inner body 1630, rather than the outer body 1620. The cooperation of the second features 1626,1636 substantially reduces the possibility of the inner body 1630 becoming unlocked from the outer body 1620 during axial insertion of the anchor 1610 into the bone. After insertion of the anchor 1610 into bone, a threaded inner member is rotationally inserted into the cavity 1631 via the use an inner member on the delivery device 1700, similar to the method of repair described above. During rotational insertion of the inner member into the cavity 1631, the cooperation of the first features 1625,1635 substantially reduces the possibility of rotation of the inner body 1630 in relation to the outer body 1620. The pointed distal portion 1634 of the inner body 1630 allows for insertion of the anchor 1610 into bone without having to create a hole in the bone prior to insertion.

For the purposes of this disclosure, the inner body 1630 is made from a metal material and the outer body 1620 is made from a polymer material. The outer and inner bodies 1620,1630 are coupled to each other via an interference fit or overmolding. However, other materials and manners of coupling may be used.

FIGS. 53 and 54 show an anchor 1900 similar to the anchor 600, albeit with a distal portion 1920 that is pointed enough to allow for insertion of the anchor 1900 into bone without first creating a hole in bone.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An anchor assembly comprising:
a rigid anchor defining a cavity, an opening to the cavity having a bottom surface, a through hole, a tapered distal end and a headless insertion member partially disposed within the anchor cavity, the insertion member including a cannulation extending a substantial length of the insertion member and threads located along an outer surface of the insertion member from a proximal end to a distal end; wherein the anchor cavity includes threads extending from the cavity opening a substantial length of the cavity, and wherein the entire through hole is proximally separated from the bottom surface; and wherein the through hole intersects the cavity, defining first and second openings on opposing sides of the cavity, the insertion member threads and cavity threads configured to engage each other and move the insertion member so as to cover the first and second openings when in a suture fixation position; and wherein the anchor is configured for a suture to be disposed within the through hole, such that the insertion member is proximal to the suture upon placement of the suture within the through hole.

2. The anchor assembly of claim 1 wherein slots extend an entire distance between openings of the through holes and a proximal end of the anchor.

3. The anchor assembly of claim 1 wherein the anchor includes a closed-ended distal end.

4. The anchor assembly of claim 1 wherein the cannulation is triangular-shaped.

5. The anchor assembly of claim 1 wherein the insertion member is non-tapered.

6. The anchor assembly of claim 1 further comprising depressions located adjacent the threads at the cavity opening.

7. The anchor assembly of claim 1 wherein in the suture fixation position, the entire insertion member is recessed within the anchor cavity.

8. An anchor assembly comprising:
an anchor defining a cavity including threads extending from an opening of the cavity and depressions located adjacent the threads at the cavity opening and extending along a wall of the cavity, and a through hole intersecting the cavity and proximally spaced from a cavity bottom surface, defining first and second openings on opposing sides of the cavity; and
a headless, non-tapered insertion member at least partially disposed within the anchor cavity, the insertion member including a threaded body and a cannulation extending a substantial length of the insertion member, the threaded body configured to engage the anchor cavity threads and move the insertion member so as to cover the first and second openings when the insertion member is in a suture fixation position; and wherein the insertion member includes a proximal portion having an opening and a flat distal portion, the flat distal portion located opposite the bottom portion of the cavity; wherein the anchor assembly is configured for a suture to be disposed within the through hole, the insertion member threadingly engaged with the cavity threads and adjacent the through hole during placement of the suture within the through hole.

9. The anchor assembly of claim 8 wherein the anchor includes a rigid body.

10. The anchor assembly of claim 8 wherein slots extend an entire distance between the through hole and a proximal end of the anchor.

11. The anchor assembly of claim 8 wherein the anchor has a pointed distal end.

12. The anchor assembly of claim 8 wherein the anchor has a closed-ended distal end.

13. The anchor assembly of claim 8 wherein the cannulation is triangular shaped.

14. An anchor assembly comprising:
a rigid anchor defining a cavity including threads, a proximal opening to the cavity, a through hole located through the anchor cavity, proximally spaced from a cavity bottom surface and intersecting the cavity so as to define first and second openings on opposing sides of the cavity; and
a headless, cannulated insertion member including threads extending along an outer surface of the insertion member extending from a proximal end, the insertion member threads configured to engage threads of the anchor cavity and move the insertion member so as to cover the first and second openings when the insertion member is located in a suture fixation position; and wherein the anchor assembly is configured for a suture to be disposed within the through hole with the insertion member disposed within the anchor cavity and adjacent the through hole.

15. The anchor assembly of claim 14 wherein the insertion member is non-tapered.

16. The anchor assembly of claim 14 wherein slots are located on opposite sides of the anchor and each slot extends an entire distance between openings to the through hole and a proximal end of the anchor.

17. The anchor assembly of claim 14 wherein the anchor has a closed-ended distal end.

18. The anchor assembly of claim 14 wherein the cannulation is triangular shaped.

* * * * *